United States Patent
Greenhalgh et al.

(10) Patent No.: US 9,962,178 B2
(45) Date of Patent: May 8, 2018

(54) PRE-LOADED INVERTING TRACTOR THROMBECTOMY APPARATUSES

(71) Applicant: STRYKER CORPORATION, Fremont, CA (US)

(72) Inventors: E. Skott Greenhalgh, Gladwyne, PA (US); Michael P. Wallace, Pleasanton, CA (US); Robert Garabedian, Mountain View, CA (US)

(73) Assignee: STRYKER CORPORATION, Fremont, CA (US)

( * ) Notice: Subject to any disclaimer, the term of this patent is extended or adjusted under 35 U.S.C. 154(b) by 0 days. days.

(21) Appl. No.: 15/496,668

(22) Filed: Apr. 25, 2017

(65) Prior Publication Data

US 2017/0303942 A1    Oct. 26, 2017

Related U.S. Application Data

(60) Provisional application No. 62/327,024, filed on Apr. 25, 2016, provisional application No. 62/345,152, (Continued)

(51) Int. Cl.
*A61B 17/22* (2006.01)
*A61B 17/221* (2006.01)
(Continued)

(52) U.S. Cl.
CPC ...... *A61B 17/221* (2013.01); *A61B 17/22012* (2013.01); *A61B 17/22031* (2013.01);
(Continued)

(58) Field of Classification Search
CPC .............. A61M 25/0119; A61M 39/06; A61M 2039/062; A61B 17/22012; A61B 17/221;
(Continued)

(56) References Cited

U.S. PATENT DOCUMENTS 4,243,040 A    1/1981   Beecher
4,863,440 A    9/1989   Chin
(Continued)

FOREIGN PATENT DOCUMENTS

GB        2498349      7/2013
WO     WO 00/32118    6/2000
(Continued)

OTHER PUBLICATIONS

Non-Final Office Action for U.S. Appl. No. 15/496,570, filed Aug. 9, 2017.
(Continued)

*Primary Examiner* — Son Dang
(74) *Attorney, Agent, or Firm* — Vista IP Law Group LLP

(57) ABSTRACT

Mechanical thrombectomy apparatuses including an inverting, rolling conveyor region ("tractor") at the distal end that are configured to grab and remove thrombus material. In particular, described herein are mechanical thrombectomy apparatuses that are adapted to prevent premature deployment of the tractor, e.g., by including a tractor hold (e.g., a housing, a lock, a clamp, etc.) or the like to secure the outer end of the tractor against and/or relative to the elongate inversion support.

15 Claims, 16 Drawing Sheets

Related U.S. Application Data filed on Jun. 3, 2016, provisional application No. 62/357,677, filed on Jul. 1, 2016.

(51) Int. Cl.
*A61M 39/06* (2006.01)
*A61M 25/01* (2006.01)
*A61B 17/00* (2006.01)
*A61B 17/34* (2006.01)
*A61B 90/00* (2016.01)

(52) U.S. Cl.
CPC ... *A61B 17/22032* (2013.01); *A61M 25/0119* (2013.01); *A61M 39/06* (2013.01); *A61B 2017/00349* (2013.01); *A61B 2017/00367* (2013.01); *A61B 2017/00831* (2013.01); *A61B 2017/2215* (2013.01); *A61B 2017/22038* (2013.01); *A61B 2017/22079* (2013.01); *A61B 2017/3435* (2013.01); *A61B 2090/037* (2016.02); *A61M 2039/062* (2013.01)

(58) Field of Classification Search
CPC ........ A61B 17/22032; A61B 17/22031; A61B 2017/00831; A61B 2017/22079; A61B 2017/00367; A61B 2017/3435; A61B 2017/22038; A61B 2017/2215; A61B 2017/00349; A61B 2090/037
See application file for complete search history.

(56) References Cited

U.S. PATENT DOCUMENTS

| | | | | |
|---|---|---|---|---|
| 4,946,440 A * | 8/1990 | Hall | ............ | A61B 18/08 600/569 |
| 5,389,100 A | 2/1995 | Bacich et al. | | |
| 6,221,006 B1 * | 4/2001 | Dubrul | ............ | A61B 17/221 600/159 |
| 9,351,747 B2 * | 5/2016 | Kugler | ............ | A61B 17/22031 |
| 9,463,035 B1 * | 10/2016 | Greenhalgh | ............ | A61B 17/221 |
| 9,717,514 B2 * | 8/2017 | Martin | ............ | A61B 17/221 |
| 2005/0085826 A1 | 4/2005 | Nair et al. | | |
| 2005/0187570 A1 * | 8/2005 | Nguyen | ............ | A61B 17/221 606/159 |
| 2006/0089533 A1 | 4/2006 | Ziegler et al. | | |
| 2006/0195137 A1 | 8/2006 | Sepetka et al. | | |
| 2006/0200221 A1 * | 9/2006 | Malewicz | ............ | A61F 2/966 623/1.11 |
| 2007/0112374 A1 * | 5/2007 | Paul, Jr. | ............ | A61F 2/013 606/200 |
| 2007/0149996 A1 * | 6/2007 | Coughlin | ............ | A61F 2/013 606/200 |
| 2007/0213765 A1 | 9/2007 | Adams et al. | | |
| 2010/0249815 A1 * | 9/2010 | Jantzen | ............ | A61B 17/22031 606/159 |
| 2011/0288529 A1 * | 11/2011 | Fulton | ............ | A61M 25/0084 604/510 |
| 2013/0046332 A1 * | 2/2013 | Jones | ............ | A61B 17/22032 606/200 |
| 2013/0096571 A1 | 4/2013 | Massicotte et al. | | |
| 2013/0317589 A1 * | 11/2013 | Martin | ............ | A61F 2/06 623/1.2 |
| 2013/0345739 A1 * | 12/2013 | Brady | ............ | A61B 17/221 606/200 |
| 2014/0005712 A1 | 1/2014 | Martin et al. | | |
| 2014/0257253 A1 * | 9/2014 | Jemison | ............ | A61B 17/32056 606/1 |
| 2015/0005781 A1 * | 1/2015 | Lund-Clausen | ............ | A61B 17/221 606/127 |
| 2015/0018860 A1 * | 1/2015 | Quick | ............ | A61B 17/320725 606/159 |
| 2015/0164666 A1 * | 6/2015 | Johnson | ............ | A61B 17/221 623/1.15 |
| 2015/0190155 A1 | 7/2015 | Ulm, III | | |
| 2016/0022293 A1 * | 1/2016 | Dubrul | ............ | A61B 17/221 606/194 |
| 2017/0086864 A1 | 3/2017 | Greenhalgh et al. | | |
| 2017/0303939 A1 | 10/2017 | Greenhalgh et al. | | |
| 2017/0303947 A1 | 10/2017 | Greenhalgh et al. | | |
| 2017/0303948 A1 | 10/2017 | Wallace et al. | | |
| 2017/0348014 A1 | 12/2017 | Wallace et al. | | |

FOREIGN PATENT DOCUMENTS

| | | |
|---|---|---|
| WO | WO 2012/009675 | 1/2012 |
| WO | WO 2012/049652 | 4/2012 |
| WO | WO 2017/058280 | 4/2017 |
| WO | WO2017189535 | 11/2017 |
| WO | WO2017189591 | 11/2017 |
| WO | WO2017189615 | 11/2017 |
| WO | WO2017210487 | 12/2017 |

OTHER PUBLICATIONS

PCT International Search Report and Written Opinion for International Appln. No. PCT/US2017/029440, Applicant Stryker Corporation, filed Jul. 7, 2017.
PCT Invitation to Pay Additional Fees for International Appln. No. PCT/US2017/029366, Applicant Stryker Corporation, filed Jul. 7, 2017.
PCT International Search Report and Written Opinion for International Appln. No. PCT/US2017/029472, Applicant Stryker Corporation, filed Jul. 7, 2017.
PCT International Search Report and Written Opinion for International Appln. No. PCT/US2017/035543, Applicant Stryker Corporation, filed Aug. 14, 2017.
PCT International Search Report and Written Opinion for International Appln. No. PCT/US2017/029366, Applicant Stryker Corporation, filed Aug. 29, 2017.
International search report and written opinion dated Feb. 28, 2018 for PCT/US2017/029345, Applicant Stryker Corporation 26 pages.
PCT Invitation to Pay Additional Fees for International Appln. No. PCT/US2017/029345, Applicant Stryker Corporation, dated Oct. 17, 2017.
Non-Final Office Action for U.S. Appl. No. 15/496,786, dated Nov. 1, 2017.
PCT International Search Report and Written Opinion for International Appln. No. PCT/US2017/050933, Applicant Stryker Corporation, forms PCT/ISA/210, 220, and 237, dated Nov. 10, 2017 (16 pages).
Response to Non-Final Office Action for U.S. Appl. No. 14/496,786, filed Feb. 1, 2018.

* cited by examiner

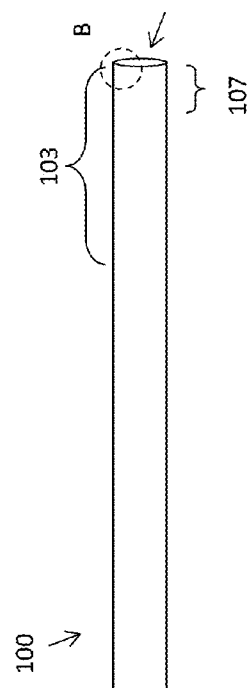
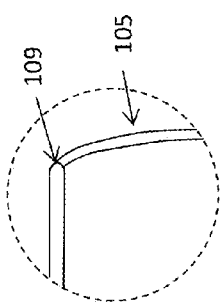
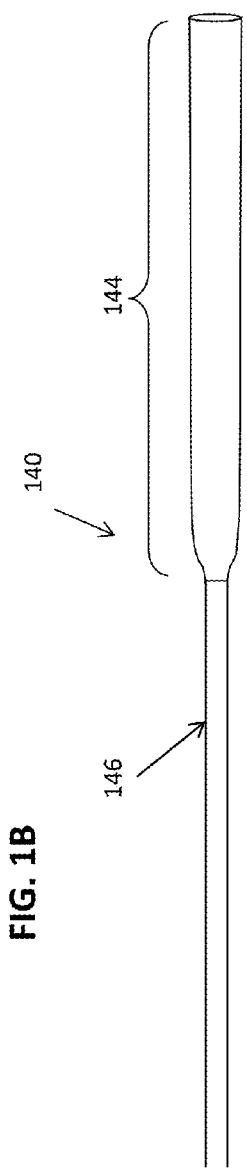
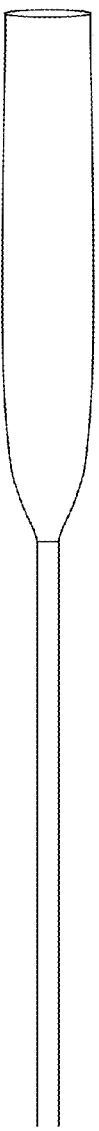
FIG. 1A
FIG. 1B
FIG. 1C
FIG. 1D

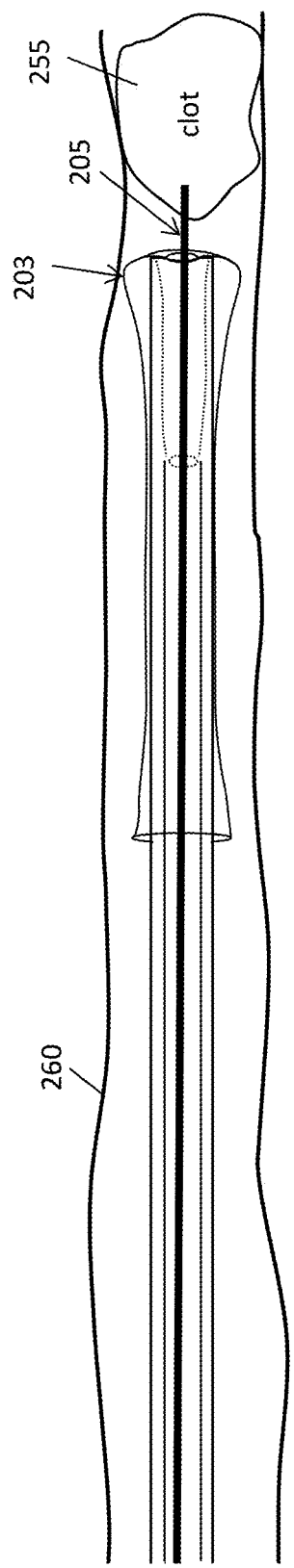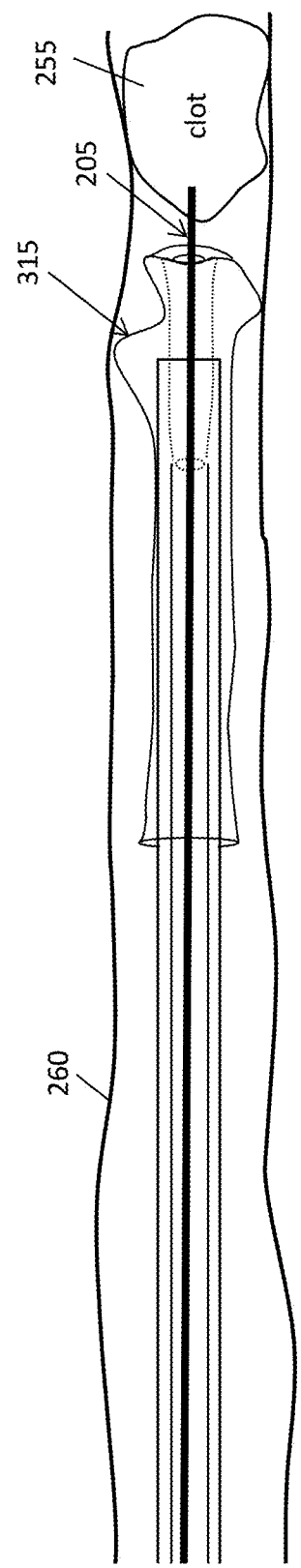

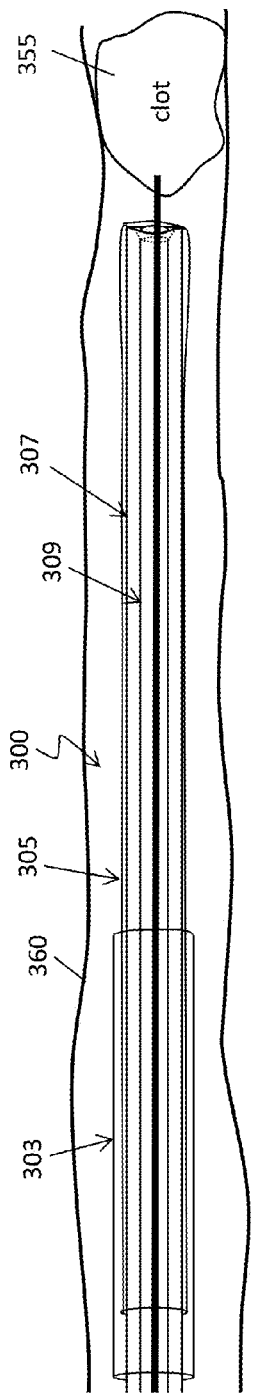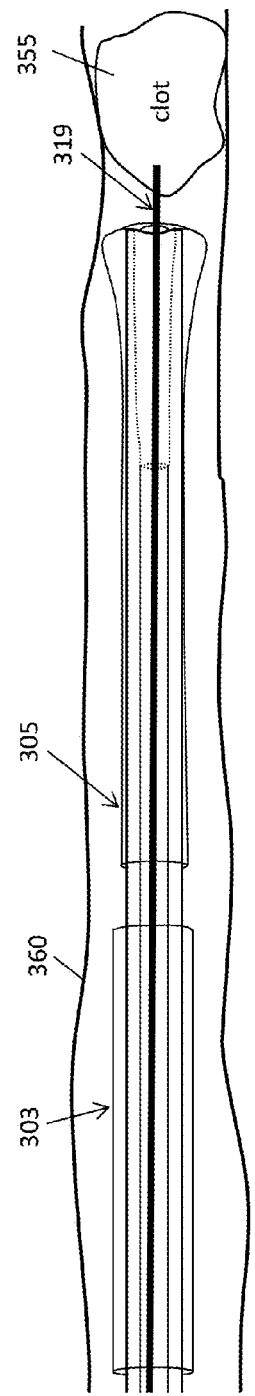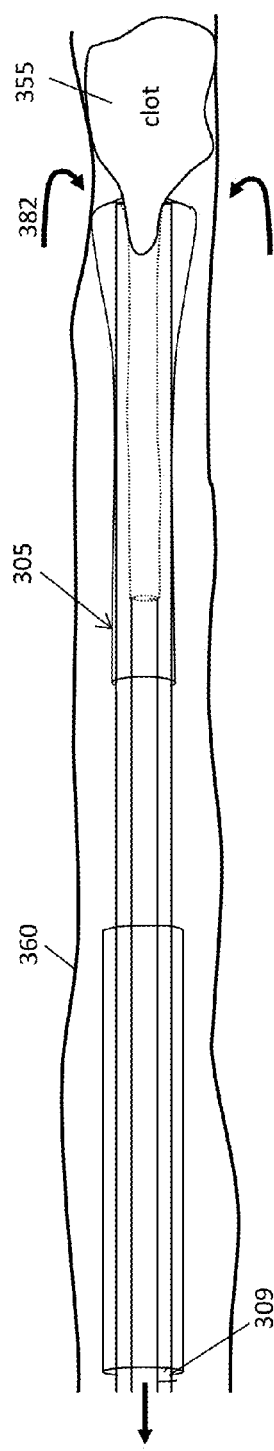

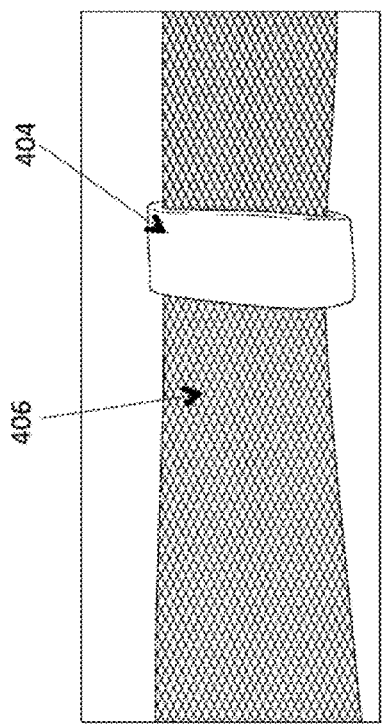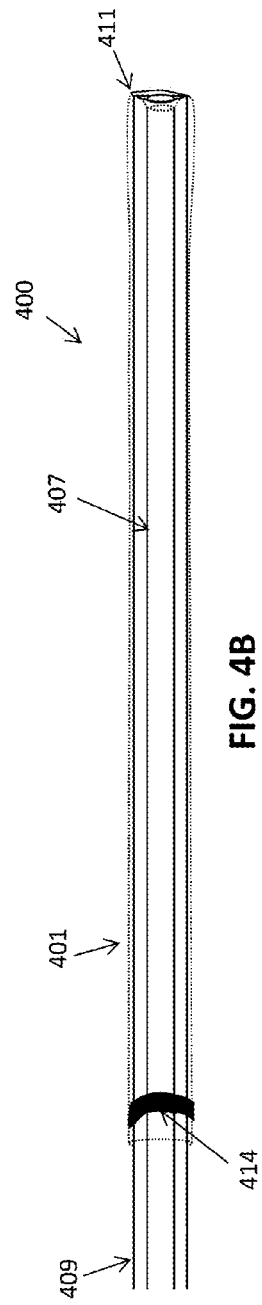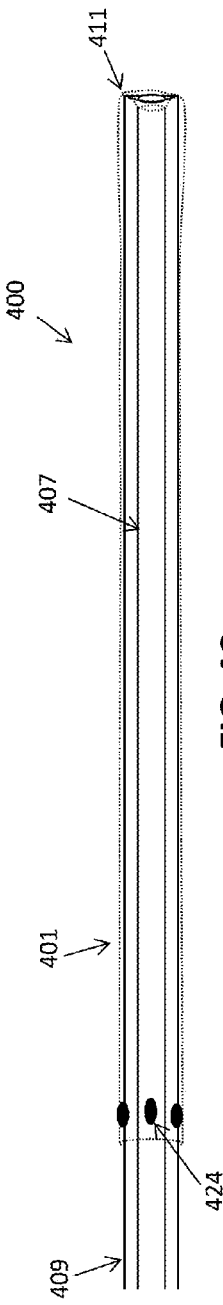
FIG. 4A
FIG. 4B
FIG. 4C

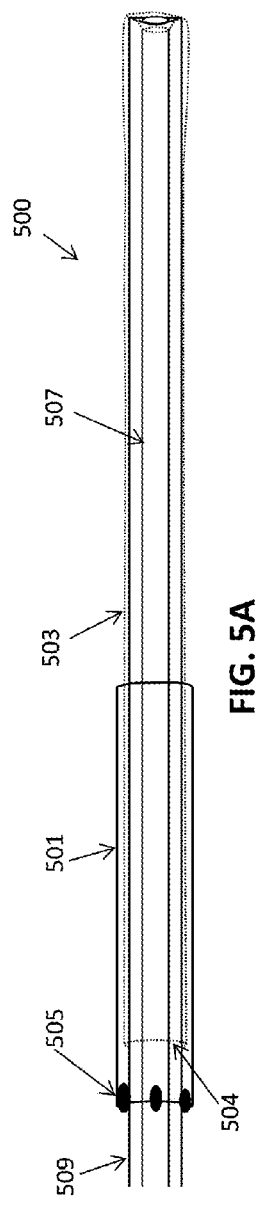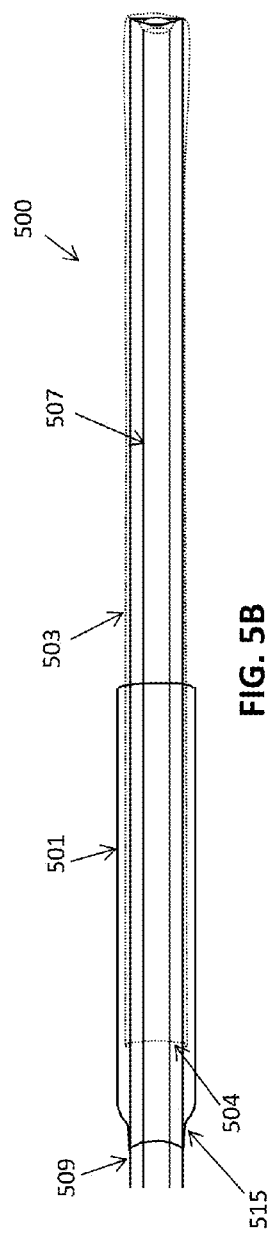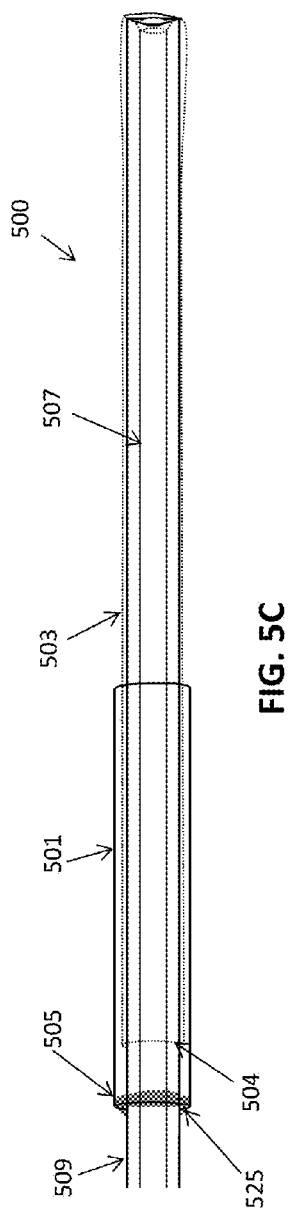

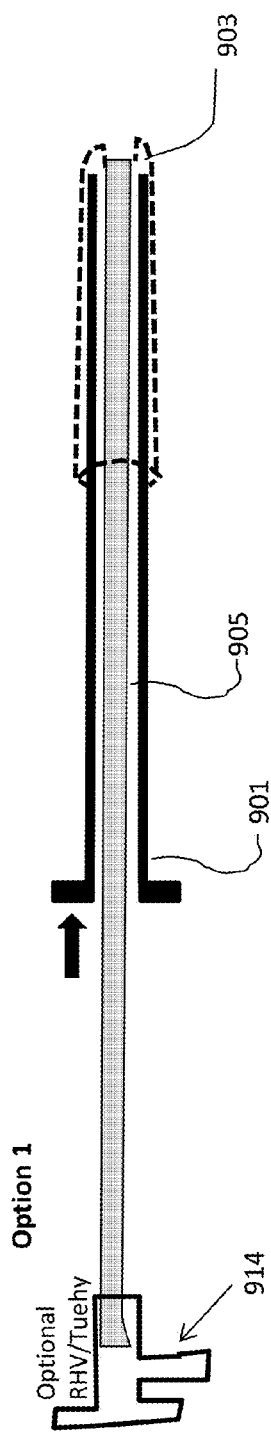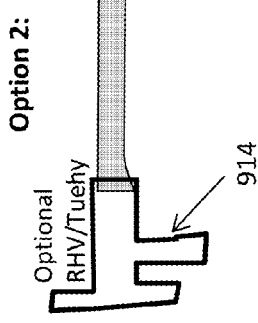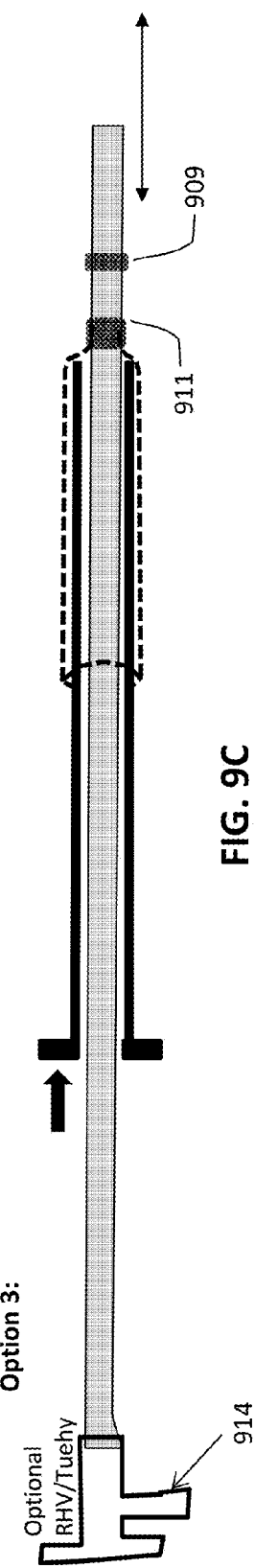

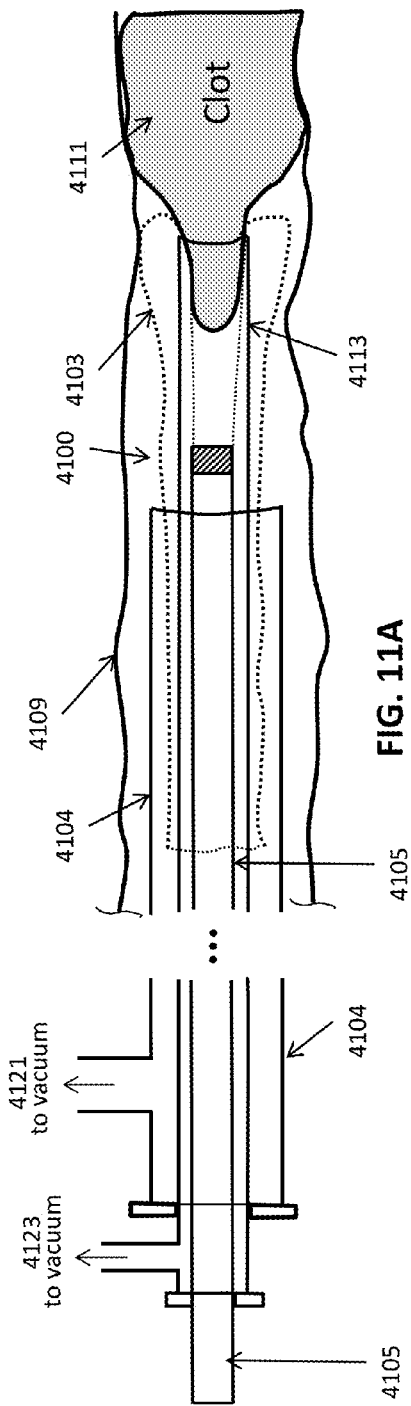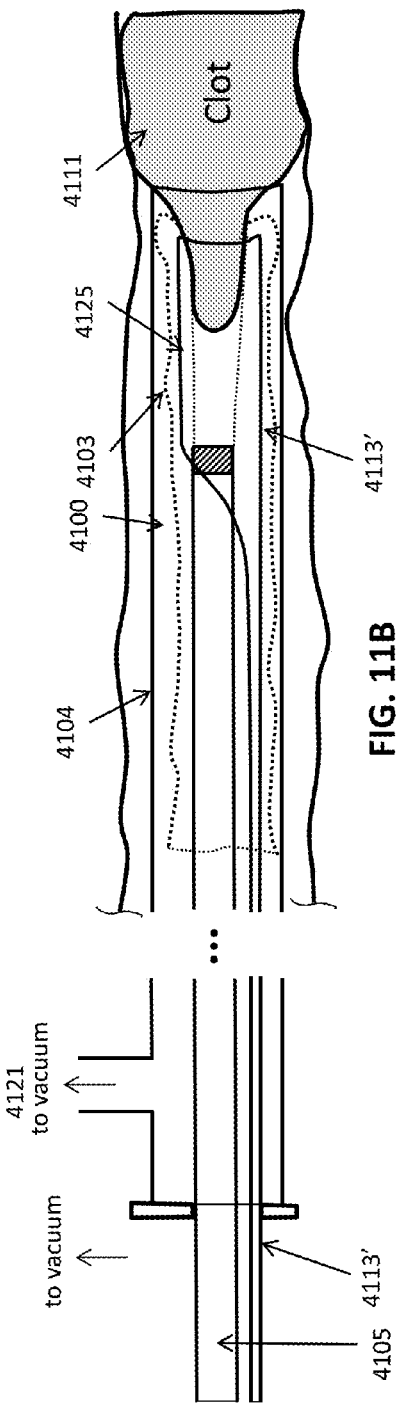

PRE-LOADED INVERTING TRACTOR THROMBECTOMY APPARATUSES

CROSS REFERENCE TO RELATED APPLICATIONS

This patent application claims priority to U.S. provisional patent application No. 62/327,024, filed on Apr. 25, 2016 and titled "DOZER THROMBECTOMY SYSTEM"; U.S. provisional patent application No. 62/345,152, filed on Jun. 3, 2016, and titled "DOZER THROMBECTOMY SYSTEM 2"; and U.S. provisional patent application No. 62/357,677, filed on Jul. 1, 2016, and titled "DOZER THROMBECTOMY SYSTEM 3".

This patent application may be related to U.S. patent application Ser. No. 15/291,015, filed on Oct. 11, 2016, titled "MECHANICAL THROMBECTOMY APPARATUSES AND METHODS", which is a continuation of U.S. patent application Ser. No. 15/043,996, filed Feb. 15, 2016, now U.S. Pat. No. 9,463,035, which claims priority to each of the following provisional patent applications: U.S. Provisional Patent Application No. 62/284,300, filed Sep. 28, 2015; U.S. Provisional Patent Application No. 62/284,752, filed Oct. 8, 2015; and U.S. Provisional Patent Application No. 62/245,560, filed Oct. 23, 2015.

Each of these patents and patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relate to mechanical removal of objects from within a body. In particular, described herein are mechanical thrombectomy apparatuses and methods.

BACKGROUND

It is often desirable to remove tissue from the body in a minimally invasive manner as possible, so as not to damage other tissues. For example, removal of tissue from within a vasculature, such as blood clots, may improve patient conditions and quality of life.

Many vascular system problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery.

When a thrombus forms, it may effectively stop the flow of blood through the zone of formation. If the thrombus extends across the interior diameter of an artery, it may cut off the flow of blood through the artery. If one of the coronary arteries is 100% thrombosed, the flow of blood is stopped in that artery, resulting in a shortage of oxygen carrying red blood cells, e.g., to supply the muscle (myocardium) of the heart wall. Such a thrombosis is unnecessary to prevent loss of blood but can be undesirably triggered within an artery by damage to the arterial wall from atherosclerotic disease. Thus, the underlying disease of atherosclerosis may not cause acute oxygen deficiency (ischemia) but can trigger acute ischemia via induced thrombosis. Similarly, thrombosis of one of the carotid arteries can lead to stroke because of insufficient oxygen supply to vital nerve centers in the cranium. Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Clinical data indicates that clot removal may be beneficial or even necessary to improve outcomes. For example, in the peripheral vasculature, inventions and procedures can reduce the need for an amputation by 80 percent. The ultimate goal of any modality to treat these conditions of the arterial or venous system is to remove the blockage or restore patency, quickly, safely, and cost effectively. This may be achieved by thrombus dissolution, fragmentation, thrombus aspiration or a combination of these methods.

Mechanical thrombectomy devices may be particularly advantageous. Depending on the size, location and extent of a clot, it may also be particularly advantageous to mechanical retrieve and break apart the clot in a manner that is both safe and effective. There is a definite need for a thrombectomy device, and particularly a mechanical thrombectomy device that can be more effective in removing tissue such as clots from within a body. Described herein are apparatuses (devices, systems and kit) and methods of using them that may address the needs and problems discussed above.

SUMMARY OF THE DISCLOSURE

Described herein are mechanical thrombectomy apparatuses (devices, methods, systems, etc.) that include a distal inverting tube of highly flexible material, referred to herein as a tractor, that is pulled to continuously invert over a distal opening, such as the distal end of a catheter or annulus, in a rolling manner. This rolling can be used, alone or on conjunction with a vacuum or mechanical thrombus (e.g., "clot") grabber, to grab, capture and remove a clot from a vessel. As mentioned, the tractor may be formed of a material having many openings and may therefore be flexible, and loose, and may be biased so as to flare open within the vessel when deployed. Prior to positioning the apparatus for grabbing the clot, it may be particularly desirable to prevent the tractor from deploying (e.g., sliding axially axially, expanding, etc.) so as to allow accurate tracking within the body as well as to ensure reliable operation of the device. Thus, it may be helpful to pin or hold the tractor, and particularly the end of the tractor that has not been inverted (e.g., within a catheter and/or within the tractor itself) prior to deployment. However, holding or and/or retaining the tractor prior to deployment must be properly balanced. If too much force is required to deploy the tractor, the force may cause the apparatus to kink, collapse, and/or jam. If the tractor can be deployed with too little force may deploy prematurely. Further, since the apparatus is likely to be used in highly tortious vessels of the body, including arteries such as the internal carotid artery, it must be retained in a manner that does not inhibit overall flexibility of the device, or trigger premature release when navigating through the vessels.

In general, an inverting tractor apparatus may include a tractor (e.g., tractor region, tractor portion, etc.) comprising a flexible tube of material that inverts as it rolls over itself at a distal end. The inverting/rolling portion may be performed over an annulus that may be separately maneuvered relative to the tractor; the annual may be part of a catheter (e.g., the distal end of a catheter) or may be attached to a wire or other element having sufficient column strength to prevent the annulus (distal opening) over which the tractor is inverting from being collapsed or pulled proximally as the tractor is rolled.

In operation, the tractor inverts and may roll back into itself. When an outer catheter is used, the tractor may be drawn into the catheter. The annulus about which the tractor inverts at the distal end region of the apparatus is supported by a structure (e.g., rod, hypotube, catheter) that typically is more rigid (has a much larger column strength) than the tractor. Thus, as the tractor rolls, it produces a conveyor-like motion as a formerly outward-facing tractor region rolls around to become an inward-facing region within the lumen of the tractor and/or within the lumen of the catheter. This conveyor or rolling motion may draw a clot (or other object) from a vessel into the catheter.

The mechanical thrombectomy apparatuses described herein include pre-loaded inverting tractor thrombectomy apparatuses (e.g., devices, systems, etc.). These apparatuses may be configured to prevent premature release of the tractor. Any of these apparatuses may include, for example, a tractor hold that prevents the end of the tractor that is "outside" of the inner lumen from sliding axially and inverting until deployment. The tractor hold may include a housing, and particularly a housing extends only a slight distance proximally (therefor preventing increasing the stiffness of the apparatus or otherwise inhibiting maneuverability/tracking). The tractor hold may include hydrophobic and/or hydrophilic surfaces, e.g., coatings, on the outside end region of the tractor and/or the outer portion of a catheter over which the tractor rolls; these hydrophobic/hydrophilic surfaces may be arranged in a pattern. Any of the tractor holds described herein may include a releasable attachment, such as an adhesive, a mechanical attachment such as a clamp or interference region or the like. Any of the tractor holds may include a pair of engaging portions, such as a stop or hold (e.g., a tractor hold or stop element on the catheter) and a lock (e.g., a tractor lock, such as a ring on the end region of the tractor).

As mentioned, any of these apparatuses may include an inverting annuls that may be part of an elongate member having sufficient column strength to resist collapsing or deflecting when the tractor is pulled proximally through the annuls to roll over and invert. The annulus may be the distal end of a catheter, or a portion of a catheter, or it may be a ring or cylindrical region to which an elongate support (e.g., wire, rod, hypotube, or any combination of these, including concentric or sequential arrangements). The annulus is typically a ring-shaped opening (the opening of which may be any shape, including but not limited to round, oval, triangular, square, rectangular, etc.), over which the tractor is inverted, and this annulus is typically connected to an elongate supporting member. The annulus may be integral with the elongate supporting member. The annulus and elongate support member may together be referred to as an elongate inversion support. As mentioned this elongate inversion support may generically be referred to herein as a catheter, which may include a tube, rod, hypotube, wire, shaft, etc. having an annuls or distal end opening over which the tractor is inverted so that the tractor rolls over the distal end opening (annulus) when an end of the tractor that is more radially positioned in the apparatus is pulled proximally. Also described herein are a variety of elongate inversion supports (e.g., catheters), as the shape (e.g., outer diameter) of the inverting support may affect the retention of the tractor prior to deployment.

For example, described herein are mechanical thrombectomy apparatuses for removing a clot from a vessel that include: an elongate inversion support (e.g., a catheter) having a proximal end and a distal end and a distal annulus (e.g., distal end opening); a tractor comprising a flexible tube that extends within the catheter, inverts over the distal end opening of the catheter and extends over the distal end of the catheter, wherein the tractor is configured to invert by rolling over the distal end opening of the catheter when a first end of the tractor is pulled proximally within the catheter; a puller coupled to first end of the tractor, wherein the puller extends within the catheter to the proximal end of the catheter; and a tractor hold attached to an outer diameter of the catheter proximal to the distal end of the catheter, wherein the tractor hold secures a second end of the tractor that extends over the distal end of the catheter until a force greater than a threshold force is applied by pulling the first of the tractor proximally within the catheter. Any of these apparatuses may include a guidewire lumen extending through the catheter, the puller and the tractor, and configured to pass a guidewire.

In any of these variations, the tractor hold may be a housing. The housing may be a cylinder that is pinned or closed on one (e.g., the proximal) end, leaving an annular opening for the outermost end of the tractor.

The tractor hold may not extend to the proximal end of the catheter. For example, the tractor hold may extend proximally along the catheter for less than 10 cm (e.g. for less than 9 cm less than 8 cm, less than 7 cm, less than 6 cm, less than 5 cm, etc.).

In any of these variations, the tractor hold may compress the tractor against the catheter. Typically, the threshold force for the tractor hold is determined by the force required to deploy the tractor within the lumen, which may depend upon the length of the apparatus, the diameter of the tractor and/or catheter, and the materials of the tractor and elongate inversion support (e.g., catheter). For example, the tractor hold may be configured to hold the second end of the tractor until the threshold force is applied, wherein the threshold force is between 50 g force and 2000 g force (e.g., between 50 g of force and 1700 g of force, between 50 g of force and 1500 g of force, between 40 g of force and 1000 g of force, between 50 g of force and 500 g of force, between 100 g of force and 500 g of force, between 200 g of force and 500 g of force, between 250 g of force and 500 g of force, between 50 g of force and 450 g of force, between 100 g of force and 450 g of force, between 100 g of force and 400 g of force, between 200 g of force and 400 g of force, etc.). The range of force appropriate to the threshold force may be important in proper functioning of the apparatus, particularly when the force is applied by pulling proximally on the puller and/or tractor; too little force for the threshold and the tractor will prematurely deploy; too much force and the apparatus will jam (e.g., by kinking the elongate inversion support).

In any of the variations described herein, the tractor may be biased to collapse and/or expand. For example, the tractor may be biased to collapse over the catheter outer diameter (e.g., the outer diameter of the elongate inversion support, including the distal end of the catheter); such tractors may also be biased to expand after inverting (e.g., within the catheter) over the distal end opening of the elongate inversion support. This arrangement may cause the tractor to form a distal-facing region that flares, trumpet-like, towards a clot distal to the device, which may help in capturing the clot and also may prevent jamming of the tractor. Alternatively or additionally, some or all of the tractor regions may be configured to expand over the outer diameter of the elongate inversion support.

The proximal end of the tractor hold may be attached to the catheter. The tractor hold may be fixed, fused, or integrally formed with the catheter.

In any of these variations, the catheter (elongate inversion support) may include comprises a larger outer diameter region and a smaller outer diameter region that is proximal to the larger outer diameter region; the annulus (distal end opening) may be at the distal end of the elongate inversion support. The the tractor hold may secure the tractor at one or more of: over the smaller outer diameter region, and between the larger outer diameter region and the smaller outer diameter region. The outer diameter of the tractor hold may be flush with the larger outer diameter region. The tractor hold may reside in a narrowing (necked) region of the catheter to avoid forming a larger-diameter region. Any of these elongate inversion supports (e.g., catheters) having regions of different diameter may have a gradual (angled) or rapid (e.g., stepped) transition between the larger outer diameter and the smaller outer diameter.

The tractor hold may comprise one or more of: a polyether block amide, a polyolefin, a polyethylene, a polypropylene, a polyethylene terephthalate (PET), and a Polytetrafluoroethylene (PTFE).

The apparatus may include a tractor lock on the second end of the tractor, wherein the tractor lock engages with the tractor hold to secure the tractor lock on a proximal side of the tractor hold until the threshold force is applied by pulling the first of the tractor proximally within the catheter. For example, the tractor lock may be a ring affixed to the end region of the tractor. The tractor lock may be a band configured to slide over the outer diameter of the catheter. The tractor hold may be a projection extending from the outer diameter of the catheter. Either or both the tractor lock and tractor hold may be elastic (e.g., compliant, rubbery, etc.) so that pulling above the threshold deployment force may cause the tractor tractor lock to release from the tractor hold.

For example, described herein are mechanical thrombectomy apparatuses for removing a clot from a vessel, the apparatus comprising: a catheter having a proximal end and a distal end and a distal end opening, wherein the catheter comprises a larger outer diameter region and a smaller outer diameter region that is proximal to the larger outer diameter region; a tractor comprising a flexible tube that extends within the catheter, inverts over the distal end opening of the catheter and extends over the distal end of the catheter, wherein the tractor is configured to invert by rolling over the distal end opening of the catheter when a first end of the tractor is pulled proximally within the catheter; a puller coupled to first end of the tractor, wherein the puller extends within the catheter to the proximal end of the catheter; and a tractor hold on an outer diameter of the catheter proximal to the distal end of the catheter, wherein the tractor hold secures a second end of the tractor that extends over the distal end of the catheter until a force greater than a threshold force is applied by pulling the first of the tractor proximally within the catheter, further wherein the tractor hold secures the tractor at one or more of: over the smaller outer diameter region, and between the larger outer diameter region and the smaller outer diameter region.

Also described herein are methods of removing a clot using a mechanical thrombectomy apparatus. These methods may include: positioning a distal end of the mechanical thrombectomy apparatus adjacent to a clot within a vessel, wherein the mechanical thrombectomy apparatus includes a tractor region that extends along a distal region of a catheter and inverts over a distal end of the catheter so that a first end of the tractor extends proximally within the catheter; disengaging a second end of the tractor from a tractor hold that secures the second end of the tractor to an outer diameter of the catheter by applying a first force that is greater than a threshold force (threshold deployment force) to the first end of the tractor; pulling the distal end of the tractor proximally within the catheter to roll the tractor over the distal end of the catheter so that the tractor inverts over the distal end of the catheter; and drawing the clot into the catheter with the inverting tractor.

Disengaging the second end of the tractor from the tractor hold may include disengaging the second end of the tractor from a tractor hold that is attached to an outer diameter of the catheter. For example, disengaging the second end of the tractor from the tractor hold may comprise disengaging the second end of the tractor from a tractor hold that extends proximally along the catheter for less than 10 cm.

Disengaging the second end of the tractor from the tractor hold may include disengaging the second end of the tractor from a tractor hold that is open at a distal-facing end; a proximal end of the tractor hold may be attached to the outer diameter of the catheter. Disengaging the second end of the tractor from the tractor hold may include disengaging the second end of the tractor from a tractor hold that secures the second end of the tractor over a smaller outer diameter region of the catheter that is distal to a larger outer diameter region of the catheter.

Disengaging the second end of the tractor from the tractor hold may comprise disengaging the second end of the tractor from a tractor hold that secures the second end of the tractor between a larger outer diameter region of the catheter and a larger outer diameter region of the catheter, wherein the larger diameter outer region is distal to the smaller outer diameter region. Disengaging the second end of the tractor from the tractor hold may comprise disengaging a tractor hold from a tractor lock, wherein the tractor lock is on the second end of the tractor. Disengaging the second end of the tractor from the tractor hold may include compressing either or both the tractor hold and a tractor lock on the second end of the tractor so that the tractor lock moves from a position proximal to the tractor hold to a position that is distal to the tractor hold.

As mentioned, the deployment threshold may be between 0.5 N and 50 N. For example, disengaging the second end of the tractor from the tractor hold may comprise pulling the first end of the tractor with the first force wherein the threshold force is between 1 N and 20 N.

In any of the apparatuses described herein the puller to which the tractor is coupled may be configured to extend from the distal end of the apparatus further than the tractor. In any of these apparatuses, the puller may be a tube (inner catheter, hypotube, etc.), and may be inserted into the clot, or may be used to draw a vacuum, apply an agent (e.g., anticoagulant, etc.) or the like. For example, described herein are mechanical thrombectomy apparatuses for removing a clot from a vessel that include: a catheter having a proximal end and a distal end and a distal end opening; a tractor comprising a flexible tube that extends within the catheter, inverts over the distal end opening of the catheter and extends over the distal end of the catheter, wherein the tractor is configured to invert by rolling over the distal end opening of the catheter when a first end of the tractor is pulled proximally within the catheter; a puller having a proximal end and a distal end, wherein the first end of the tractor is coupled to the puller at a region that is proximal to the distal end, further wherein the puller extends within the catheter to the proximal end of the catheter. Any of these apparatuses may include a guidewire lumen extending through the catheter, the puller and the tractor, and configured to pass a guidewire.

For example, the apparatus may further include a stop between the distal end of the puller and the distal end opening. For example, the apparatus may include a stop on the puller between the distal end of the puller and the first end of the tractor, wherein first end of the tractor is coupled to a sliding ring configured to slide over the puller until it engages the stop. Any of these apparatuses may include a 2 mm or greater distance between the distal end of the puller and the region of the puller to which the first end of the tractor is coupled.

As mentioned, the proximal end of the puller may be configured to couple to a vacuum source. For example, the proximal end of the puller may include a valve, e.g., a Tuohy-Borst valve/rotating hemostasis valve (RHV).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1H illustrate an example of an apparatus for mechanically removing an object such as a clot form a body region. FIG. 1A shows an example of an elongate inversion support portion of an apparatus, configured as a catheter portion. For example, at least the distal end of the elongate inversion support may be configured as a catheter. FIG. 1B shows an enlarged view of a distal end (opening) of the catheter of the elongate inversion support of FIG. 1A, showing the aperture formed by the distal end opening; FIG. 1C shows an example of a distal tractor region of a flexible tube (tractor tube) extending from a puller (the puller in this example is configured as a catheter. The tractor is shown in a first (e.g., un-inverted) configuration) and may be biased open, e.g., by heat setting, to have an outer diameter that is greater than the inner diameter of the catheter of the elongate inversion support, as shown in FIG. 1D. FIG. 1D shows the same distal tractor region of FIG. 1C with the expandable first end region expanded. This first configuration may be compressed down into the elongate inversion support and the distal end inverted over the catheter portion of the elongate inversion support, as shown in FIG. 1E. In FIG. 1E, the assembled mechanical thrombectomy apparatus with the elongate inversion support and the flexible tube forming the tractor is shown. The tractor extends through the catheter of the elongate inversion support and doubles back over the distal end opening of the catheter and extends over the outer diameter of the catheter. The outer portion of the tractor (extending along the outer diameter of the catheter) may be held in a collapsed configuration (as shown in FIG. 1E), or it may be expanded, as shown in FIG. 1F. Thus, the tractor may be biased so that in the second configuration (inverted over the distal end of the catheter), the tractor has a 'relaxed' outer diameter that is greater than the outer diameter of the catheter of the elongate inversion support. FIGS. 1G and 1H illustrate the use of the apparatus of FIGS. 1E and 1F to remove a clot by drawing the flexible tube proximally and/or advancing the catheter distally towards the clot so that the expandable first end region inverts as it is drawn into the distal end of the catheter, pulling the clot into the catheter.

In FIG. 1I, the tractor is shown attached to the distal end of a tapered or narrow puller; the distal end region is tapered, and includes a radiopaque marker at or near the attachment site to the tractor; the tractor may be knitted, braided, woven, etc. Thus, in some variations the distal end region of the puller may have a greater flexibility than the proximal end of the puller. The puller may be hollow (e.g., a catheter or hypotube) or solid (e.g., like a wire).

FIGS. 2A-2C illustrate a mechanical thrombectomy apparatus deploying prematurely within a vessel.

FIGS. 3A-3C illustrate a method of operating a mechanical thrombectomy apparatus that includes a tractor hold to prevent premature deployment.

FIGS. 4A-4C illustrate examples of mechanical thrombectomy apparatuses including a tractor hold that secures the tractor to the outer diameter of the catheter until release.

FIGS. 5A-5C illustrate examples of mechanical thrombectomy apparatus including a tractor hold as described herein.

FIGS. 7A-7B illustrate a catheter portion of an elongate inversion support having both different diameters (e.g., a larger-diameter distal catheter connected to a smaller-diameter proximal region extending longitudinally in the proximal-to-distal axis), and a plurality of openings (e.g., cut-out regions, holes, etc.). FIGS. 7C-7D illustrate a catheter of an elongate inversion support having a plurality of opening formed therethrough. FIGS. 7E-7F illustrate another variation of a catheter of an elongate inversion support having a distal catheter region and an elongate support member formed by skive cutting the catheter. FIGS. 7G-7H illustrate another variation of an elongate inversion support having a distal catheter region and an elongate support member extending from the catheter region. FIGS. 7I-7J illustrate another variation of an elongate inversion support having a plurality or openings along the distal-to-proximal length. FIGS. 7K-7L illustrate another variation of an elongate inversion support having a minimal catheter region at the distal end forming a distal end opening that is connected to an elongate support (e.g., wire, tube, bar, rod, etc.).

FIG. 8A shows the elongate inversion support. FIG. 8B shows a variation of the elongate inversion support of FIG. 8A including guide rings for the puller and tractor. FIG. 8C shows the elongate inversion support of FIG. 8B with the tractor and puller attached. FIG. 8D shows a mechanical thrombectomy apparatuses including that shown in FIG. 8C with an additional outer catheter.

FIGS. 9A-9C illustrate mechanical thrombectomy apparatuses, including apparatuses having pullers that may extend distally of the catheter (FIGS. 9B and 9C).

FIG. 11A illustrates a method for removing clot using an intermediate catheter (e.g., sleeve) and a vacuum, in which a mechanical thrombectomy apparatus is extended from a distal end of the intermediate catheter to remove a clot.

FIG. 11B illustrates a method for removing clot using an intermediate catheter (e.g., sleeve) and a vacuum, in which a mechanical thrombectomy apparatus removes a clot that has been drawn into the distal end of the intermediate catheter.

DETAILED DESCRIPTION

Figure 1E:
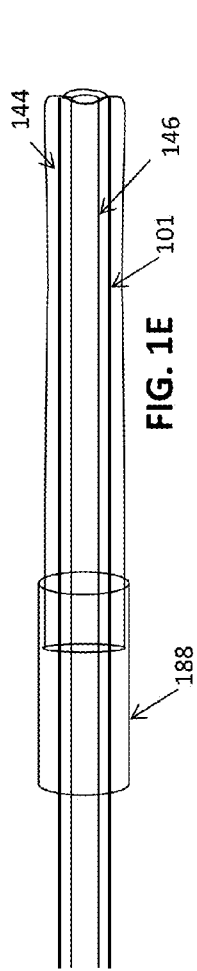

In general, described herein are mechanical thrombectomy apparatuses having an inverting tractor region and an elongate inversion support having a distal annulus over which the tractor rolls and inverts over itself. Any of these apparatuses, and methods of using them, may be configured to prevent premature deployment of the tractor. The elongate inversion support may be a catheter having a distal end opening. The tractor may comprise a flexible tube that may be formed of a sheet having openings, or may be a woven, braided, knitted, etc. material such as a fiber. The tractor may extend longitudinally within the elongate inversion support and may and double back (e.g., invert) over the annulus of the elongate inversion support (e.g., the distal end of a catheter) so that it extends along the midline of the apparatus; when the elongate inversion support is a catheter, the tractor may extend within the catheter lumen. The tractor may connect to an inner puller that is typically coupled to an end of the tractor (which may be referred to as the inner end or the distal end) that can be pulled proximally to pull and invert the tractor over the distal end so that it rolls over the distal end, which may capture a clot. The apparatus may include a guidewire lumen extending through the catheter, tractor and/or tractor puller.

In general, a mechanical thrombectomy apparatus for removing a clot from a vessel may be a system, assembly or device including an elongate inversion support having a distal end and a distal annulus, and a flexible tractor assembly at least partially inverted and configured to roll and invert over the distal annulus of the elongate inversion support.

In many of the examples described herein, the elongate inversion support is a catheter (or a portion of a catheter at the distal end) and the annulus is formed by the distal end opening of the catheter; the tractor extends within the catheter and doubles back over the distal end of the catheter to extend over the outer diameter of the catheter at the distal end of the catheter, although it may extend proximal for any appropriate distance (including between 1-30 cm, between 2-20 cm, greater than 1 cm, 2 cm, 3 cm, 4 cm, 5 cm, 6 cm, 7 cm, 8 cm, 9 cm, 10 cm, 11 cm, 12 cm, 15 cm, 20 cm, etc.). The end of the tractor within the catheter may be coupled to a pusher (e.g., at a proximate pusher region connected to the distal or inner end of the tractor). The tubular tractor may include an elongate lumen that is configured to allow passage of a guidewire. The tubular tractor may also be configured to slide along the long axis within the catheter lumen and invert over the distal end opening of the catheter when the proximal end region is pulled proximally. The tractor may be referred to herein as a tractor assembly, tractor portion, tractor tube, or simply a tractor, and is typically positioned and longitudinally slideable within the catheter, and arranged so a portion of the tractor (sometimes referred to as the "distal tractor region" or "distal-facing" tractor region) doubles back over itself.

For example, FIG. 1A shows one variation of a catheter that may form part of the apparatuses described herein. In this example, the catheter 100 includes a distal end region 103 that includes a distal end 105. The distal end region may have an increasing softness (measured by durometer, e.g., shore durometer) except that the very distal tip (distal end 105, including the distal end opening) may be substantially less soft than the region immediately proximate to it. Thus, although the distal tip region of the catheter (e.g., the distal most x linear dimensions, where x is 10 cm, 7 cm, 5 cm, 4 cm, 3 cm, 2 cm, 1 cm, 9 mm, 8 mm, 7 mm, 6 mm, 5 mm, 4 mm, 3 mm) has an increasing softness/decreasing harness extending from the proximal to distal ends, the very distal end region 107 (e.g., measured as distal most z linear dimensions, where z is 1 cm, 9 mm, 8 mm, 7 mm, 6 mm, 5 mm, 4 mm, 3 mm, 2 mm, 1 mm, 0.8 mm, 0.5 mm, 0.3 mm, 0.2 mm, etc., and z is always at least three times less than x) has a hardness that is greater than the hardness of the region immediately proximal to it, and may be as hard or harder than the proximal-most region of the distal tip region.

For example, FIG. 1A shows one variation of a catheter of an elongate inversion support that may form part of the apparatuses described herein. In this example, the elongate inversion support includes a catheter 100 having a distal end region 103 that includes a distal end opening 105. The distal end region may have an increasing softness (measured by durometer, e.g., shore durometer) except that the very distal-most end region (distal end 105, including the distal end opening) may be substantially less soft than the region immediately proximate to it. Thus, although the distal tip region of the catheter (e.g., the distal most x linear dimensions, where x is 10 cm, 7 cm, 5 cm, 4 cm, 3 cm, 2 cm, 1 cm, 9 mm, 8 mm, 7 mm, 6 mm, 5 mm, 4 mm, 3 mm) has an increasing softness/decreasing harness extending from the proximal to distal ends, the very distal end region 107 (e.g., measured as distal most z linear dimensions, where z is 1 cm, 9 mm, 8 mm, 7 mm, 6 mm, 5 mm, 4 mm, 3 mm, 2 mm, 1 mm, 0.8 mm, 0.5 mm, 0.3 mm, 0.2 mm, etc., and z is always at least three times less than x) has a hardness that is greater than the hardness of the region immediately proximal to it, and may be as hard or harder than the proximal-most region of the distal tip region.

In FIG. 1A, the elongate inversion support is an elongate hollow catheter having a column strength that is sufficient to prevent buckling when the catheter is pulled over the distal annulus (distal end opening). Thus, the elongate inversion support may be configured so that it does not collapse (e.g., buckle) when 500 g or less of of compressive force is applied (e.g., at least about 700 g, 600 g, 500 g, 400 g, 300 g, etc. of compressive force) for neurovascular applications. For peripheral vascular applications the elongate inversion support may be selected or configured to withstand at least 1500 g of compressive force (e.g., at least about 2000 g, 1900 g, 1800 g, 1700 g, 1600 g, 1500 g, 1400 g, etc. of compressive force). In general, any of the apparatuses described herein may include a elongate inversion support that is not a full-length catheter, but may include a portion of a catheter, typically at the distal end, connected to a rod, wire, hypotube, or the like (as will be described in greater detail below in reference to FIGS. 7A-8D) or may be skived. Thus, any of the apparatuses and methods described herein may be adapted for use with an elongate inversion support that is not limited to catheters, including elongate inversion supports that include a portion of a catheter, or that include a ring or other structure forming the annulus at the distal end. In FIG. 1A the catheter 100 of the elongate inversion support may be any appropriate type of catheter or portion of a catheter, including microcatheters appropriate for neurovascular use.

In some variations the distal end 105 of the elongate inversion support is adapted so that the tractor may slide or roll and invert over the distal end of the catheter without being caught (binding, jamming) or without substantial friction. For example, in some variations the distal tip (end) may be curved or radiused 109 as shown in FIG. 1B, particularly on the outer surface (e.g., the transition from outer diameter to inner diameter).

FIG. 1C shows an example of a flexible tractor 144 coupled to a puller 146. In this example to form a pullable tractor assembly 140, the tractor is shown integrated with the puller, forming the assembly. In FIG. 1C, the tractor is a tube of material (e.g., wove, knitted, braided, etc.) that is flexible and elongate. The tractor is shown extended from the puller in a first configuration. It may be particularly beneficial if the relaxed outer diameter of the flexible tractor in this first configuration has a greater outer diameter than the outer diameter of the catheter of the elongate inversion support into which the tractor will be positioned prior to inverting. The flexible and tubular tractor 144 may be sufficiently soft and flexible (e.g., having a low collapse strength) so as to easily roll and fold over the distal aperture of the elongate inversion support. The puller 146 may typically be a less-expandable (or non-expandable) structure (tube, puller, etc.). In the example shown in FIG. 1C, the tractor 144 is configured, e.g., by shape-setting (heat setting, etc.), to expand in the relaxed first configuration to a radial diameter that is between 1.1 and 10 times the diameter of the inner diameter of the catheter of the elongate inversion support when unconstrained, as shown in FIG. 1D. In FIG. 1D, the tractor of FIG. 1C is shown in an expanded, relaxed, configuration. Thus the expandable tractor may be biased to expand open. The tractor may be formed of a mesh, braided, woven, knitted, or sheet of material and is generally adapted to grasp the object to be removed (e.g., blood clot).

In FIGS. 1C and 1D the tractor and puller have two portions, a tractor 144 and a less expandable (or non-expandable) proximal portion comprising the puller 146. The puller may be a separate region, such as a wire, catheter or hypotube, which is connected to an end region of the tractor (e.g., a flexible mesh, woven, braided, etc.), e.g., the distal end or near the distal end. The inverting region of the tractor, where it rolls and inverts over the distal end opening of the catheter may be referred to as the distal-facing region of the tractor, which may actively grab clot when rolling.

Figure 1F:
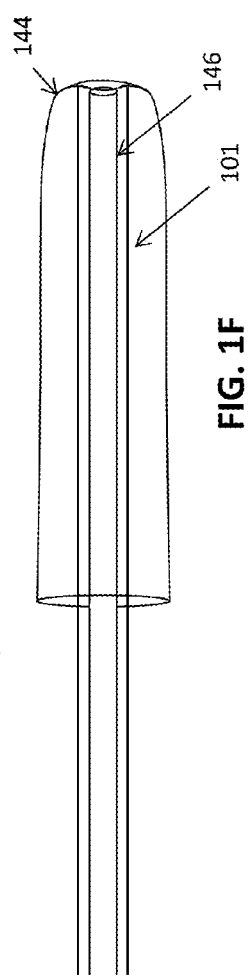

In FIG. 1E, the flexible tractor of FIG. 1C is shown with the tractor doubled back over itself an over the the distal end of the catheter of the elongate inversion support 101. The distal end region is collapsed down, e.g., onto the puller and the elongate inversion support, and may be held collapsed. In this example a tractor hold 188 may be used to hold the tractor collapsed down onto the outer diameter of the elongate inversion support. However, in an unconstrained or deployed configuration, as shown in FIG. 1F, the tractor in this second configuration (e.g., the portion that is inverted over the distal end of the catheter) has an outer diameter that is greater than the outer diameter of the catheter of the elongate inversion support. Thus, the tractor 144 may be biased so that it has a relaxed expanded configuration in the first configuration (as shown in FIG. 1C) that is greater than the inner diameter (ID) of the catheter of the elongate inversion support portion of the apparatus and the relaxed expanded configuration of the second configuration (shown in FIG. 1F) inverted over the catheter has an OD that is greater than the OD of the catheter. The tractor is expandable and may be coupled to the puller. In some variations the flexible tractor and the puller may comprise the same material but the tractor may be more flexible and/or expandable, or may be connected to a push/pull wire or catheter.

Figure 1G:
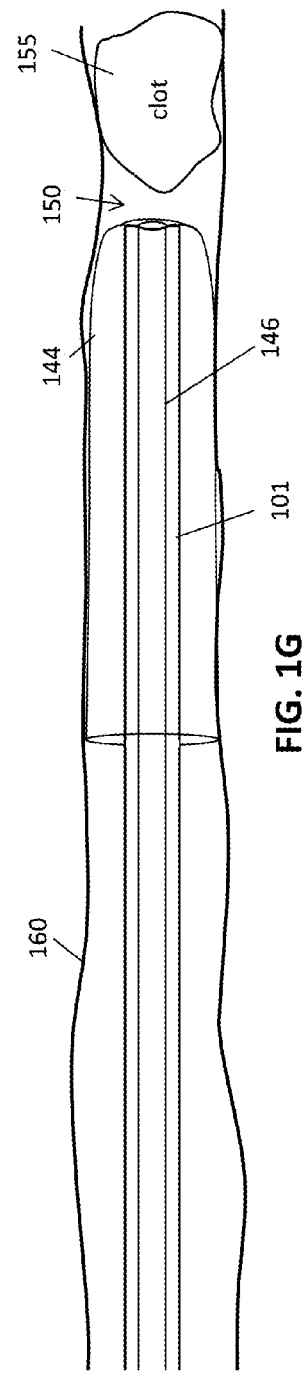
Figure 1H:
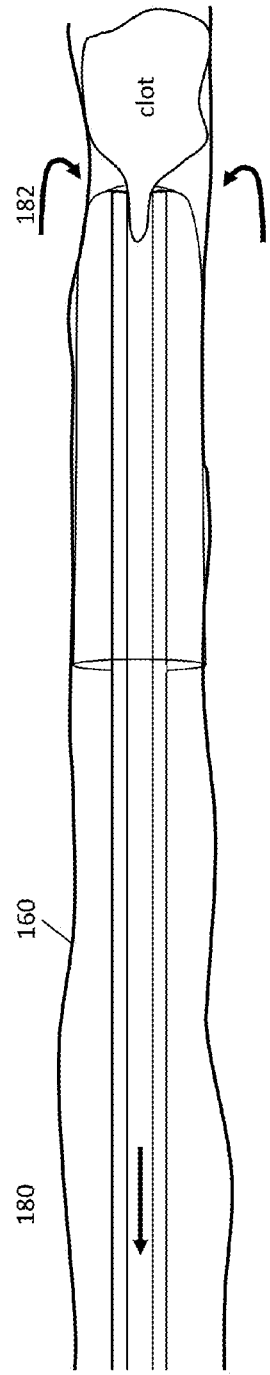
Figure 1I:
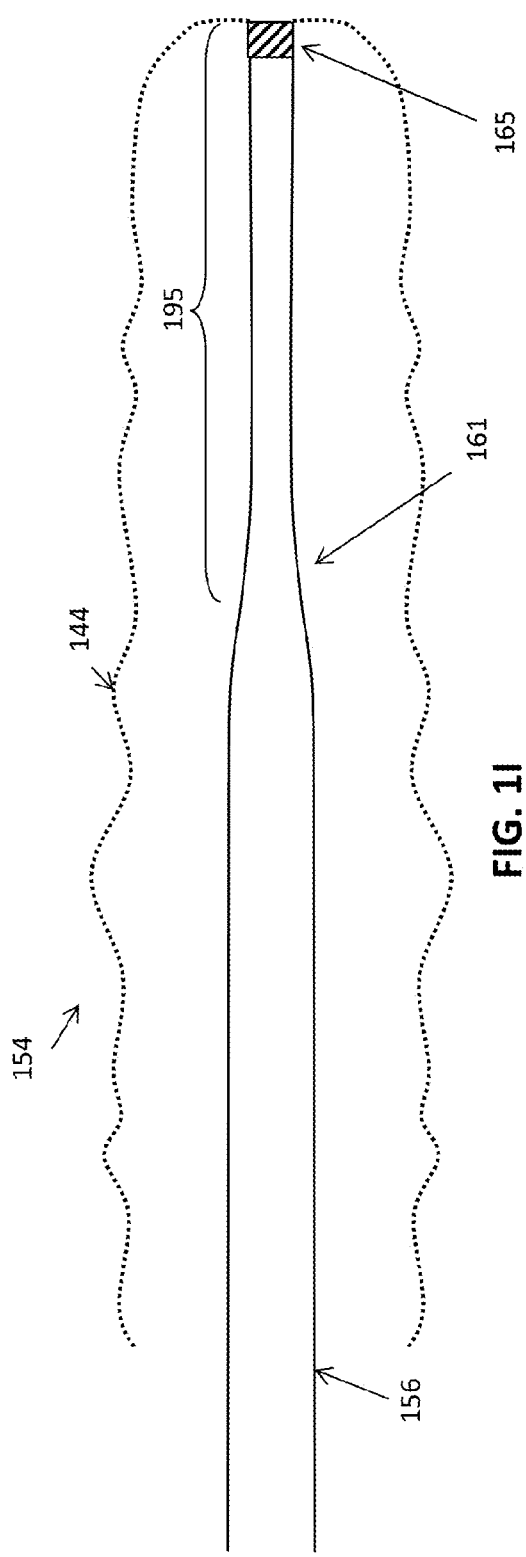
FIG. 1I illustrates an alternative variation of a tractor and puller.

FIGS. 1G and 1H illustrate the removal of a clot using an apparatus such as the apparatus assembled from the components of FIGS. 1A and 1E. In this example the apparatus is configured as a thrombectomy apparatus including a catheter of an elongate inversion support 101 and a flexible tractor that extends over the distal end region of the catheter and doubles-over itself at the distal end of the catheter to invert so that the external tractor end region is continuous with an inner less-expandable (in this example, less-expandable includes non-expandable) second distal end region 146 (puller) that extends proximally within the catheter and forms an inner lumen that may pass a guidewire. The pusher/puller member that may be a rod or other member that is continuous with the distal end region of the tractor. In FIG. 1G the apparatus is shown positioned and deployed within the vessel 160 near a clot 155. The clot may be drawn into the catheter by pulling the tractor 140 proximally into the catheter 101, as indicated by the arrow 180 showing pulling of the inner portion of the flexible tractor (e.g., using a handle, not shown) resulting in rolling the tractor over the end opening of the catheter and into the catheter distal end and inverting the expandable distal end region so that it is pulled into the catheter, shown by arrows 182. The end of the tractor outside of the catheter may be "loose" relative to the outer wall of the catheter. FIG. 1I illustrates another example of a tractor assembly 154 including a tractor 144 that is coupled to a puller 156. The puller in this example is tapered (having tapering region 161) and may therefore have a different flexibility of the distal end region than the proximal end region. For example the proximal end region may be less flexible than the narrower-diameter distal end region 195 to which the tractor is coupled. The assembly includes a radiopaque marker 165. The tractor may be attached to the puller by any appropriate means. For example, the tractor may be crimped, glued, fused, or otherwise attached to the puller, typically permanently.

These apparatuses may be highly flexible, both before actuating and during operation. For example, in general, the flexible tractor may not increase the stiffness/flexibility of the catheter, and particularly the distal end region of the catheter too much, to avoid impacting maneuverability, particularly within tortious vessels of the neurovasculature. Described herein are flexible tractor tube portions that increase the stiffness of the last y cm (e.g., distal most 20 cm, 18 cm, 15 cm, 12 cm, 10 cm, 9 cm, 8 cm, 7 cm, 6 cm, 5 cm, 4 cm, 3 cm, 2 cm, 1 cm, etc.) of the catheter less than a predetermined percentage (e.g., less than 10%, 12%, 15%, 18%, 20%, 25%, 30%, etc.). For example, described herein are flexible tractor tube portions that pass through the catheter and double back over the distal end of the catheter but increase the stiffness of a distal 5 cm of the catheter by less than 15% of the stiffness of the distal 5 cm of the catheter without the flexible tube extending therethrough and doubling back over the distal end of the catheter.

In any of the apparatuses described herein, in which the tractor is at least partially inverted over the distal end of the catheter so that the tractor extends on the outer surface of the catheter, the tractor may be releasably coupled to the outer diameter of the catheter to allow the apparatus to be inserted through a body, including through tortious vessels in the body, prior to being deployed to remove a clot or other element from the vessel. The tractor may be a braided, woven or knit material tube of material that is inverted over the distal end of the catheter; alternatively the tractor may be formed of a sheet of material that include openings therethrough.

Any of the apparatuses described herein may be adapted to prevent premature deployment of the tractor, e.g., by including a tractor hold (e.g., a housing, a lock, a clamp, etc.) or the like to secure the outer end of the tractor against and/or relative to the elongate inversion support. For example, a tractor hold may secure the outer end of the tractor against a catheter into which the tractor inverts when pulled proximally by the puller.

Figure 2A:
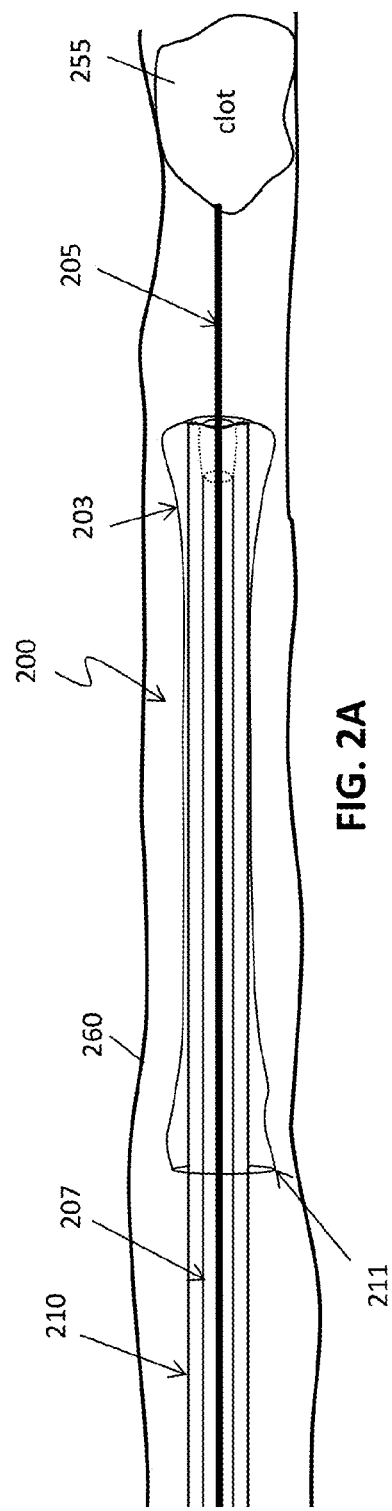

An example of premature deployment is shown in FIGS. 2A-2C. For example, in FIG. 2A, the tractor 200 is guided over a guidewire 205 to a clot 255 (alternatively, the apparatus may be delivered without using a guidewire). In this example, the apparatus includes a tractor 203 that extends over and into a catheter 210. The inner end of the tractor is connected to a puller 207 (shown in this example as an inner catheter). The outer end 211 of the catheter is loose and is shown slightly expanded over the catheter outer diameter. As the apparatus is advanced distally towards the clot, shown in FIG. 2B, the tractor is, by virtue of being deployed, driven into the catheter prematurely, shortening the length of the tractor that is outside of the catheter and available to roll for capture of the clot. Further, the loose outer end of the tractor may interfere with accurate positioning of the apparatus. FIG. 2C illustrates the premature deployment compromising the rolling of the tractor 315. Once the tractor is prematurely deployed, moving it back and forth in the vessel to position it may result in the tractor, which may contact the vessel wall when deployed, folding or tangling, as shown in FIG. 2C.

In general, the apparatuses described herein are configured to prevent premature movement of the tractor on an outside, e.g., outer diameter, of the catheter during catheter access to a target location.

Any of the variations described herein may include a tractor hold that includes a sticky, tacky, gummy, or adhesive material on the tractor or between the tractor and the catheter over a portion of the tractor that is held against the outer diameter of the catheter. For example, as illustrated in FIGS. 4A-4C, the apparatus may include a sticky substance, like silicone, impregnated on the end of the tractor that is wrapped over the catheter (e.g., the outer end of the tractor, which may be referred to as the proximal-most most end of tractor). The sticky material may impregnated over a small portion of the tractor (e.g., local regions at or near the proximal end and/or discrete regions, or patterns including spots, bands, etc. along the length of the outer portion of the tractor. The presence of the sticky regions may prevent premature slipping of the tractor (e.g., braid, woven, etc.) with respect to the catheter. For example, a silicone impregnated braid may sit on or over a section of the catheter that is not coated with a hydrophilic coating before the tractor is pulled around distal end opening of the catheter, which may help prevent the tractor from prematurely slipping off or over the catheter. As mentioned, a sticky (e.g., tacky, adhesive, gummy, etc.) region may be present on the entire tractor, on just an inside surface of the tractor (e.g., the surface that faces the catheter when applied over the outer diameter of the catheter), on both inner and outer surface of the tractor, and/or in discrete locations (including patterns) of the portion of the tractor outside of the catheter. For example, the apparatus may include a plurality of regions of sticky material arranged over the length of the proximal end of the tractor. In some variations the sticky material is arranged in a pattern. The material applied may be referred to as sticky with respect to the catheter (e.g., causing temporary and/or releasable attachment between the catheter and the tractor). In some variations, the sticky material may be coated or applied to the outer diameter of the catheter. When arranged in a pattern (e.g., on the tractor and/or OD of the catheter), the pattern of sticky material locations on the tractor (and/or catheter) may be arranged in multiple, non-contiguous locations along the length or the tractor. Patterns may include stripes, spirals, rings, spots, etc.

Alternatively or additionally, the tractor may be temporarily secured to the outside of the catheter through other methods to provide a temporary attachment of the tractor to the catheter outer diameter (OD). For example, a temporary attachment may be presented between the tractor and the catheter OD such that, when axial tension if applied to the tractor, e.g., by the user pulling the tractor to pull the tractor around catheter tip, the temporary attachment (e.g., a temporary bond, temporary securement, etc.) between the tractor and the catheter OD may be released, allowing the braid to slide relative to the catheter. Alternatively or in addition to the use of a sticky material between the tractor and the catheter, temporary attachments between the tractor and the OD of catheter may include: hydrophilic coatings on the tractor and/or catheter, and/or spot (including micro-spot) boding between the catheter and the tractor.

For example a hydrophilic surface on the tractor (e.g., inner face of the tractor) and/or catheter OD may be applied as a coating. The tractor may be pre-assembled onto the catheter and a hydrophilic/hydrophobic surface may provide a temporary attachment between the catheter and the tractor. A layer of hydrophilic coating (or two adjacent layers) may secure the tractor to the catheter OD, and may help the apparatus track through a body vessel/lumen to the target location, after which the tractor may be deployed by pulling to separate the surfaces of the tractor and catheter OD, and to allow the tractor to roll over the distal end opening freely so that it may engage with a clot and draw it into the apparatus. In some variations, a hydrophilic coating may be separately applied to the tractor and/or the catheter. For example, the catheter OD and tractor may be separately coated with a hydrophilic coating and then assembled. When the apparatus is assembled (e.g., with the tractor over catheter distal end region, inverted and within the catheter), the coating on both subassemblies (e.g., tractor and catheter) may cold flow together. When the assembly is wetted in the body during catheter access and when approaching the target clot to be removed, the user may pull the tractor proximally (by pulling on the puller attached to the inner end of the tractor) which may slide the tractor with respect to the catheter OD, disengaging the tractor hold.

Alternatively the tractor hold can be formed by spot- or selectively bonding the tractor to the catheter OD. A spot or micro-bond may be adequate to prevent premature sliding of the tractor relative to the catheter OD during catheter access. For example, a spot bond or a plurality of micro-bonds can be created, e.g., by heat bonding (melting) or applying adhesive to attach the tractor to the catheter OD. The micro bonds can be placed circumferentially at several locations along the length of the braid, continuously along the braid/catheter contact length or in any other pattern, as discussed above.

FIG. 4A illustrates an example of a thermoplastic polyurethane (TPU) 404 that may be used to temporarily secure the tractor 406 to the outer diameter of the catheter; once in position, the distal end of the catheter (internal to the catheter) may be pulled proximally to break the material (in this example, pellathane) and release the tractor so that it may be rolled distally over the catheter to draw a clot into the catheter. In this example, the frangible (e.g., breakable) material is coated over a region on the catheter and/or tractor (shown here as a braided tractor) that does not include a hydrophilic coating). For example, the frangible material may be applied over a region that is masked (uncoated) from hydrophilic coating.

In FIGS. 4B and 4C, examples of mechanical thrombectomy apparatuses 400, 400' are shown, each having an outer catheter 409, and a tractor that extends over the distal end region of the catheter, and inverts over the distal end opening (annulus 411) of the catheter, and into the catheter where it connects to a puller 407. In FIG. 4B, the tractor is releasably adhered to the outer diameter of the catheter by a sticky (e.g., hydrophilic) region 414 that engages the outer end of the tractor to a region on the outer diameter of the catheter. Thus, in order to pull the tractor proximally within the catheter and therefore roll the tractor over and into the distal end opening as described above (and shown, e.g., in FIG. 3C), an initial deployment force threshold (e.g., between 0.5 N and 50 N) may be required. Once the force is applied and the tractor is deployed to axially move distally over the outer surface, roll, invert and into the catheter, the force required to continue rolling may be substantially (e.g., the deployment force threshold may be 1.1×, 1.2×, 1.5×, 1.7×, 2×, 3×, 4×, 5×, 10×, or more the force required to roll the apparatus).

Similarly, in FIG. 4C, the apparatus may include a plurality of spot attachments 424 at the outer end of the tractor. As mentioned, there spots may be an adhesive attached into (e.g., into the mesh, etc.) of the tractor, or between the tractor and the outer diameter of the catheter. In both FIGS. 4B and 4C, the tractor may be held slightly in tension over the distal end region of the catheter, preventing the tractor from deploying and expanding, including expanding at the distal tip region (forming the trumpet-shaped opening such as shown in FIGS. 2A-2B).

Alternatively or additionally, any of the apparatuses described herein may include a tractor hold that is configured as a housing or garage for holding the outer end of the tractor, as shown in FIGS. 3A-3C and FIGS. 5A-5C. In these examples the tractor hold extends only partially down the catheter, which may prevent the hold from increasing the flexibility and maneuverability of the apparatus in the lumen. FIGS. 3A-3C illustrate the method of use of a variation of a mechanical thrombectomy apparatus 300 including a tractor hold 303. In this example, the tractor hold is positioned over the catheter, as shown in FIG. 3A, and holds the outer end of the tractor 305 against the outer diameter of the catheter 307. The tractor is connected to the puller 309. The tractor hold may be attached to the catheter (e.g., at a proximal end of the hold) or it may be applied over the catheter (e.g., shrink-wrapped over the catheter and the outer end of the tractor. The apparatus 300 may be guided over a guidewire 319, as shown, or it may be directed to the clot 355 within the vessel 360 without the use of a guidewire.

Once the distal end of the apparatus is near the clot, as shown in FIG. 3A, a force greater than a deployment threshold force (e.g., the force required to pull the tractor out of the tractor hold 303, leaving the tractor hold behind, and allowing the tractor to roll 382 over the distal end opening of the catheter, as illustrated in FIG. 3C. The apparatus may be advanced distally while pulling the inner end of the tractor proximally with the puller to invert and roll the tractor into the catheter. The tractor may then grab a clot and pull it into the catheter, as shown.

Similarly, in FIGS. 5A-5C, the apparatus 500 includes a tractor 503 coupled to a puller 507 at an inner end that is within a catheter 509. In this example, the outer end 504 of the tractor is pinned against the outer diameter of the catheter by a tractor hold 501 configured as a garage or housing. The housing may hold the end of the tractor lightly or it may secure it against the catheter more tightly, depending on the desired deployment threshold. In FIG. 5A, the tractor hold is secured to the outer diameter of the catheter by a weld or welds 505. Similarly in FIGS. 5B and 5C the tractor hold is secured by either being shrunk-fit to the outer diameter at the proximal end 515, or by an adhesive or glue 525, respectively.

In all of the examples shown in FIGS. 3A-3C and 5A-5C, the tractor hold extends only slightly down the length of the catheter, e.g., a few cm (e.g., less than 10 cm, less than 9 cm, less than 8 cm, less than 7 cm, less than 6 cm, less than 5 cm, less than 4 cm, less than 3 cm, etc.).

Figure 6A:
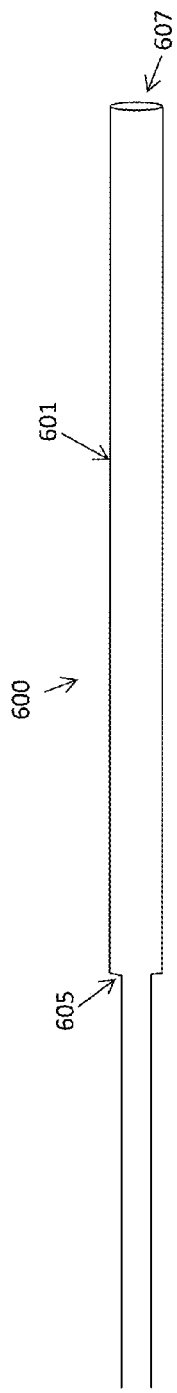
FIG. 6A illustrates a catheter for a mechanical thrombectomy apparatus with an outer diameter that steps up from a first proximal outer diameter to a second, larger distal outer diameter.
Figure 6B:
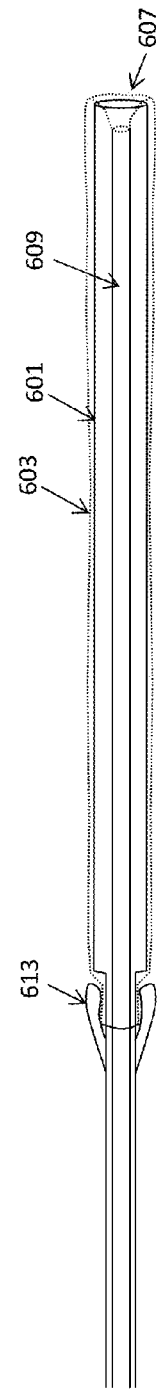
FIGS. 6B-6D illustrate the catheter of FIG. 6A as part of different mechanical thrombectomy apparatuses having tractor holds that secure the tractor to the catheter.
Figure 6C:
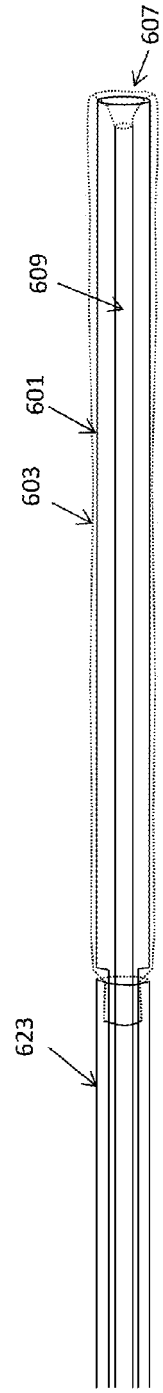

In any of the variations described herein, the elongate inversion support may have a different outer diameter along its axial (longitudinal) length. For example, although the catheter shown in FIG. 1A has a uniform diameter along its length, other apparatuses may include a catheter having a larger diameter at the distal end region than at more proximal regions, as shown in FIGS. 6A-8C. For example, in FIG. 6A, the elongate inversion support is a catheter having a larger outer diameter at the distal end than at the proximal end. The transition between the two regions is a step 605. The annular region (distal end opening 607) therefore has the same, larger, outer diameter as the distal end region. FIGS. 6B-6C, illustrates examples in which a tractor is held over the outer diameter and may be secured by a tractor hold. In general, particularly where the tractor is configured to contract down onto the tractor, simply having the transition, and particularly a rapid (including step) transition between a region of larger diameter and a region of smaller diameter, as shown in FIG. 6A, may help secure the tractor over the catheter. In FIG. 6B, the same catheter shown in FIG. 6A has had a tractor 603 attached so that it extends along the distal outer diameter region, inverts over the distal end opening 607, and into the catheter inner lumen, where it is connected to or integral with a puller 609. In FIG. 6B, the outer end of the tractor is held in place with a tractor hold 613; in this example, the tractor hold 613 is one or more arms that hold the tractor against the smaller inner diameter immediately adjacent to the step up to the larger diameter region of the catheter.

In FIG. 6B, the tractor hold is a narrower catheter 623 that extends proximally; the tractor is held between the distal opening of the tractor hold and the step up to the larger diameter catheter 601. The outer surfaces of the tractor hold and the catheter 601 may be flush, e.g., having the same height. In FIG. 6B, if the tractor hold extends proximally far enough (e.g., to or beyond the end of the catheter) it may be actively disengaged, reducing or eliminating the deployment threshold force.

Figure 6D:
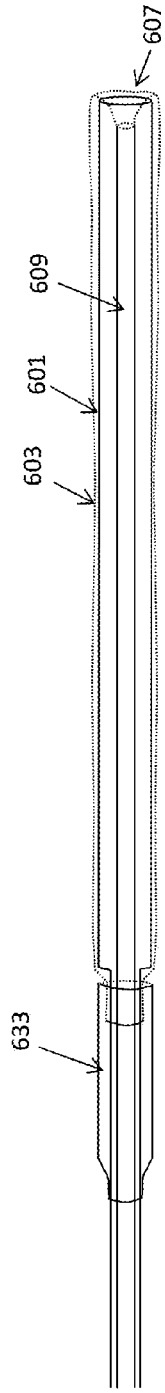

FIG. 6D shows another example of a tractor lock 633, similar to that shown in FIG. 6C, only extending partially proximally down the catheter. In any of these variations the tractor hold may be fixed to the outer diameter or it may be movable (e.g., slideable) relative to the outer diameter of the catheter.

Figure 7A:
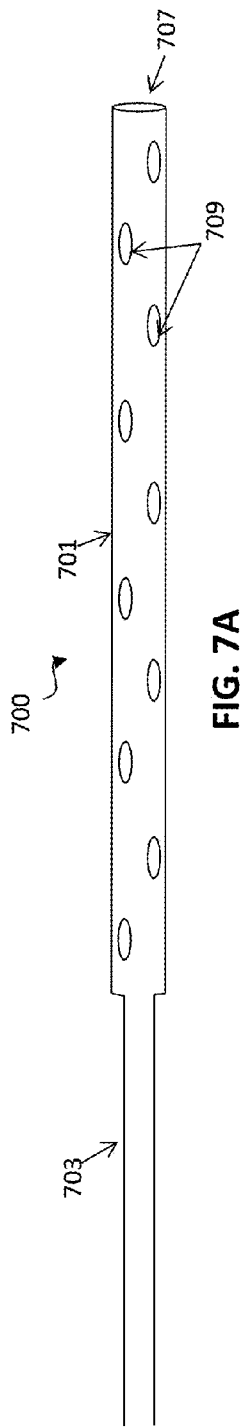
FIG. 7A-7L illustrate examples of different elongate inversion supports for mechanical thrombectomy apparatuses.
Figure 7B:
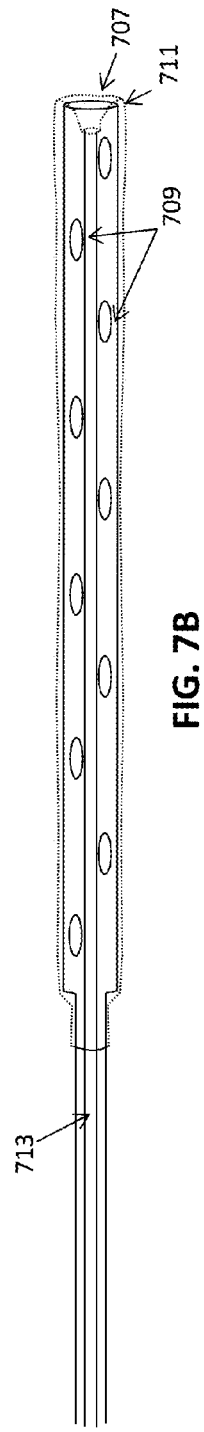

FIGS. 7A-7L illustrate different variations of catheters that may be used as part of any of the apparatuses described herein. For example, FIG. 7A shows an example of a catheter 700 having a larger-diameter distal end region that also includes a plurality of openings, slots, holes, windows, slits, etc. 709. These openings may provide for delivery of fluid (including drugs) to the site of use, and/or removal of material, e.g., the application of vacuum through the apparatus, particularly useful when used with an intermediate catheter into which the apparatus (e.g., an elongate inversion support, a puller and tractor) is inserted, as will be described in greater detail below. FIG. 7B shows the apparatus of FIG. 7A with an attached puller and tractor.

Figure 7C:
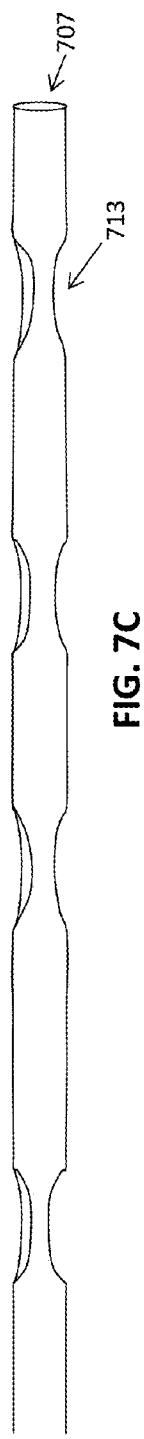
Figure 7D:
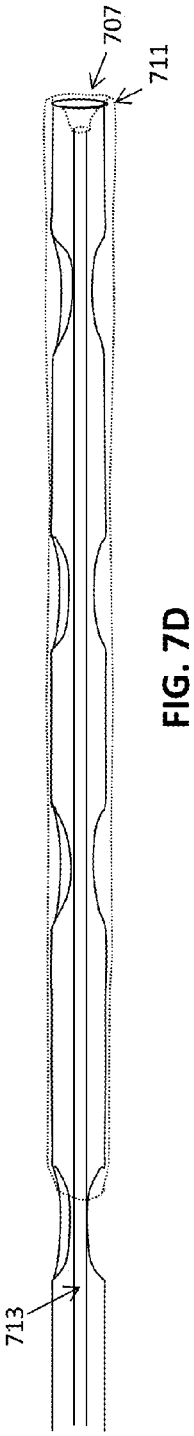
Figure 7E:
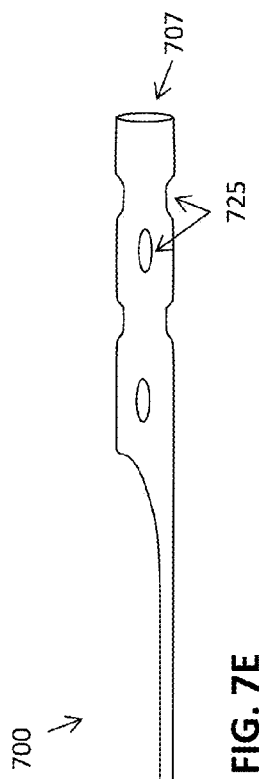
Figure 7F:
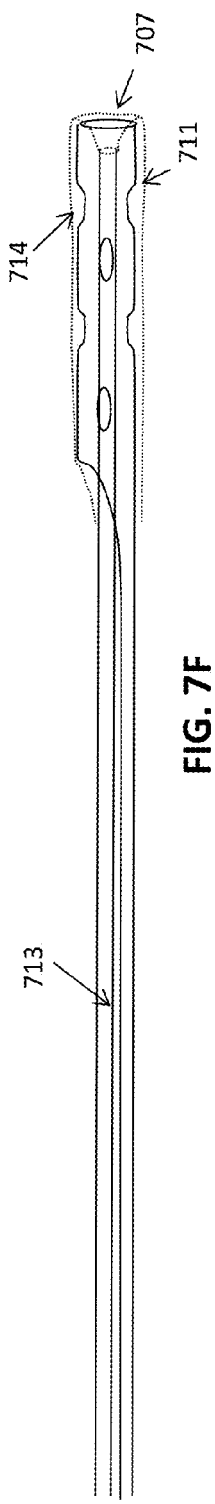
Figure 7G:
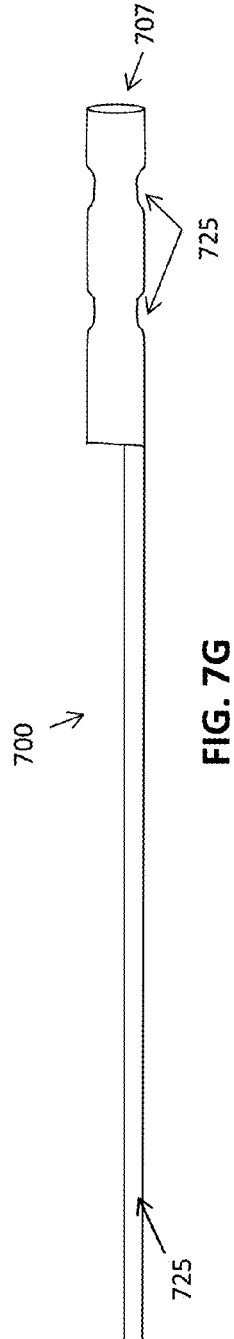
Figure 7H:
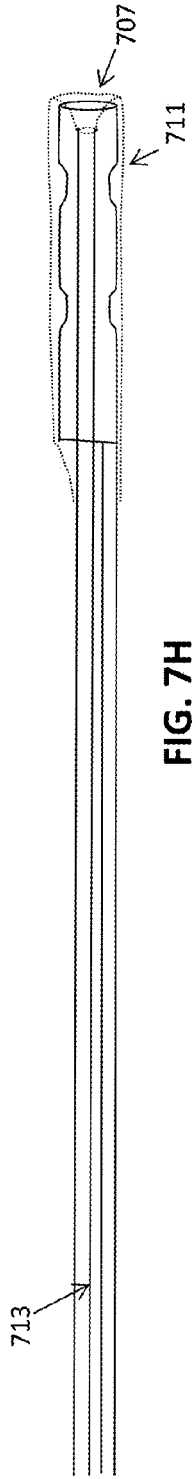

FIGS. 7C and 7D illustrate another variation of a catheter that may be used as part of any of the apparatuses described herein, including, as here, catheters that have a plurality of cut-out regions. Similarly, FIGS. 7E and 7F show an example including a catheter having a large proximal skive region, leaving the majority of the outer diameter much smaller than at the distal end region, as shown. In addition, the distal end of the catheter may include openings, slots, cut-out regions, etc. 725. FIG. 7F shows the catheter of FIG. 7E with a tractor 714 coupled on an inner end to a puller 713. The puller is still pulled within the lumen of the catheter. A similar example is shown in FIGS. 7G and 7H, however instead of being skived, the elongate inversion support includes a distal portion formed of a catheter having cut-out regions 725 that is coupled to a rod, pole, wire or (as shown) a hypotube. This hypotube may be used as a guidewire lumen and/or as a channel for a stiffening or support member that may, once the device is positioned, enhance the column strength to allow pulling of the tractor proximally when inverting the tractor to roll.

Figure 7I:
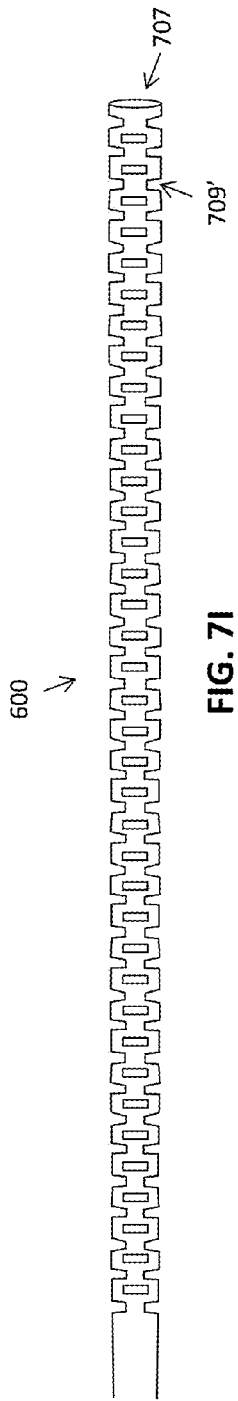
Figure 7J:
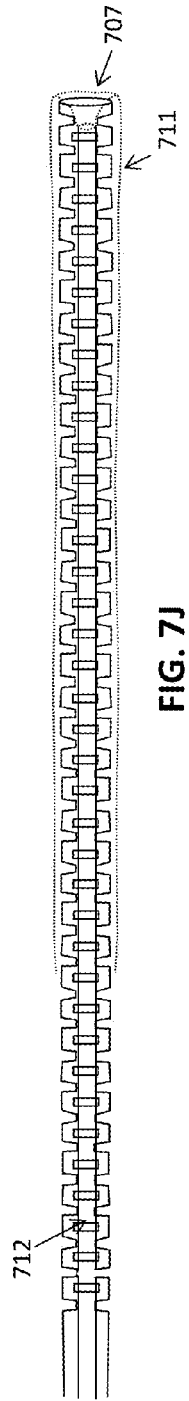

FIGS. 7I and 7J illustrate an example of a catheter (FIG. 7I) and an apparatus including the catheter (7J) in which the sides of the catheter have been slotted, which may provide enhanced flexibility while maintaining column strength. An apparatus including the catheter of FIG. 7I is shown in FIG. 7J, also including a tractor and puller.

Figure 7K:
Figure 7L:
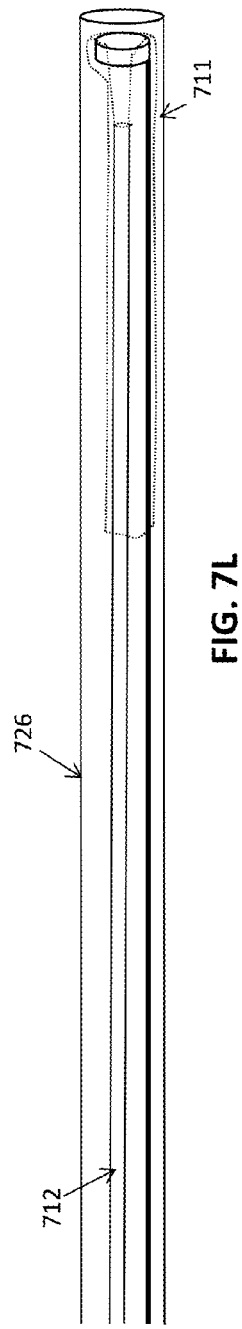

FIG. 7K is an example of an elongate inversion support in which the distal end is a cylinder 716, formed, for example, from a very small portion of a catheter. The distal end opening (annulus 707) may be used to invert the tractor, as shown in FIG. 7L. The elongate shaft 717 of the elongate inversion support may be a rod, tube, wire, etc. as described above. An additional outer catheter 726 may be included in any of these apparatuses, as shown in the exemplary apparatus shown in FIG. 7L, which includes the elongate inversion support of FIG. 7K.

Figure 8A:
FIGS. 8A-8D illustrate another example of an elongate inversion support that may be used as part of a mechanical thrombectomy apparatus.
Figure 8B:
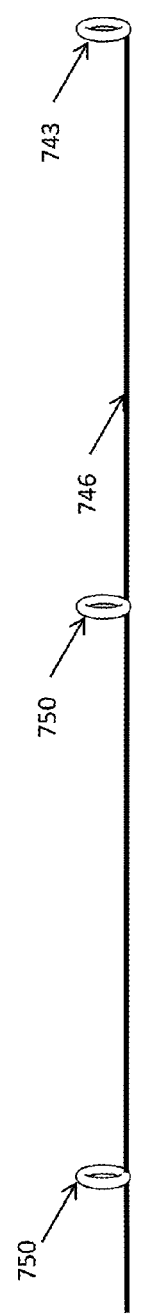
Figure 8C:
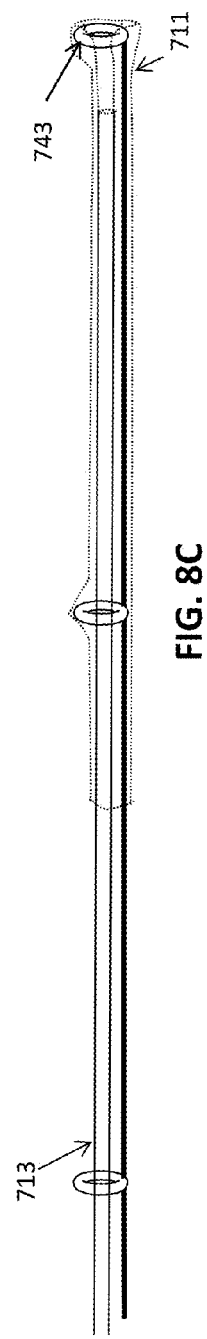
Figure 8D:
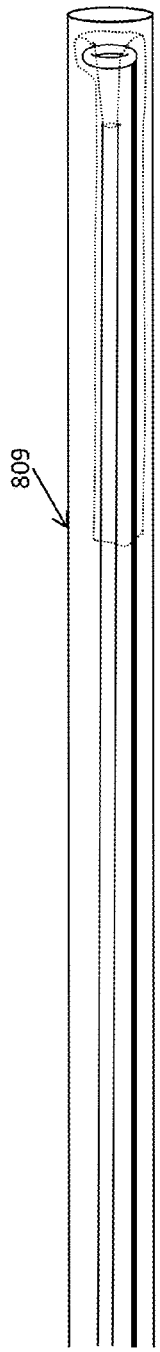

FIGS. 8A-8D also illustrate another example of an elongate inversion support having a distal annulus or aperture 743, shown in this example a ring (e.g., toroid ring) bonded to a hypotube 746 (which may alternatively be a rod, wire, small-diameter catheter, etc.); as mentioned above, a stiffening member may be inserted into the elongate body of the elongate inversion support prior to or during pulling of the tractor proximally through the distal annulus. FIG. 8B shows a similar variations of the elongate inversion support of FIG. 8A, only with a plurality of guides 750 extending down the length of the support into which the tractor puller and/or tractor may be held, as illustrated in FIG. 8C. In this example, the tractor 810 extends over the elongate inversion support and can be pulled proximally by the tractor puller 812. Although the tractor puller is shown as a catheter, in any of the apparatuses described herein, the tractor puller may instead be a wire, hypotube, etc. as mentioned above. FIG. 8D is an apparatus similar to that shown in FIG. 8C with the addition of an outer catheter 809.

Releasable Lock

Figure 10A:
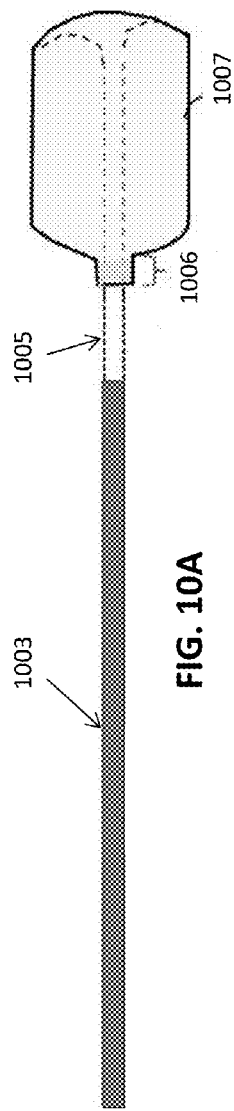
FIGS. 10A-10C illustrate an example of a mechanical thrombectomy apparatuses having a tractor hold configured to engage a tractor lock on the tractor.
Figure 10B:
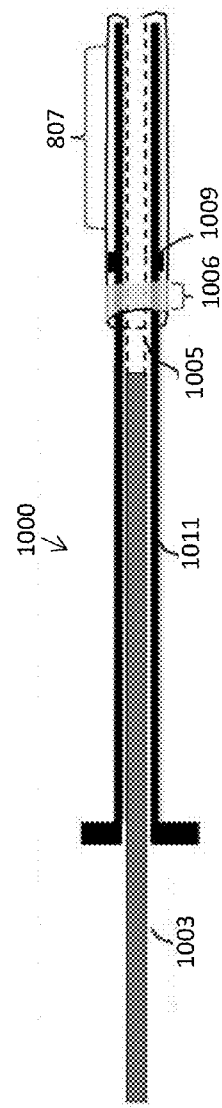
Figure 10C:
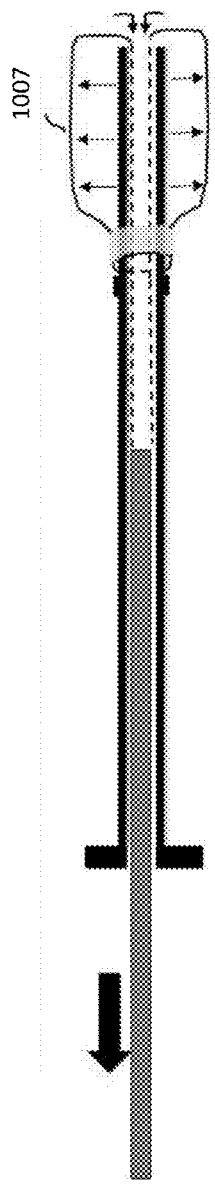

In some variations, the tractor hold and distal end region of the catheter to which it is applied over may be configured as (or may include) a releasable lock, in addition to or instead of the tractor holds described above (e.g., a sticky materials, frangible release, housing, etc.). For example, the catheter may include a tractor hold comprising a friction lock (e.g., bump, protrusion, enlarged diameter, region, O-ring, etc.) on the outer diameter of the catheter that engages with a locking region (e.g., construction, inward-pointing bump, sticky coating, etc.) on the outer (e.g., proximal) end region of the tractor. The locking region on the outer end portion of the tractor may be proximally beyond the locking region (e.g., friction bump) on the catheter, so that the catheter locking region may be initially held beneath the tractor. When force is applied (e.g., deployment force applied by the user) to pull the tractor region proximally from the inside of the tractor, the force may overcome the locking engagement between the tractor locking region (e.g., constriction, inwardly-facing protrusion, etc.) and the locking catheter locking region (e.g., friction bump, radial enlargement, O-ring, etc.) and the tractor may be released roll distally over the catheter. See FIGS. 10A-10C for an example of this arrangement. Note that this releasable lock may be used in combination with any of the features described above. In FIG. 10A-10C, the tractor 1007 includes a tractor lock 1006 at the outer end of the tractor. FIG. 10A shows just the tractor and puller 1003. The mechanical thrombectomy apparatus 1000 shown in FIG. 10B also includes a catheter 1011, and the catheter includes a tractor hold 1009. The tractor hold engages with the tractor lock; in FIG. 10B, the tractor hold is a protrusion that holds the tractor lock on the tractor on a proximal side of the tractor hold, until sufficient force is applied above the deployment threshold to deploy the tractor by pulling the tractor lock distally over the tractor hold, allowing the tractor 1007 to deploy and/or expanded, and be rolled over the distal end opening of the catheter, to capture a clot.

In any of these variations, but particularly the locking variations described herein, the tractor region may be held in tension, although tension is not necessary. Alternatively or additionally, a second outer cover or catheter may be used, or may be absent.

Apparatuses Having Distal-Extending Pullers

In any of the variations described herein, the puller may extend more distally than the tractor in the apparatus. For example, a pre-assembled apparatus having the distal end of a tractor puller (e.g., catheter, hypotube, wire, etc.) that extends more distally beyond the catheter(s) or the rest of the apparatus may be used to help capture the clot. As mentioned above, any of these variations may include the use of a vacuum, e.g., for aspirating the clot. The vacuum may be applied through the puller. It may be easier to grab onto a clot when using aspiration to initiate the grabbing.

For example, FIG. 9A illustrates an example of a mechanical thrombectomy apparatus similar to that described above. The tractor 903 is connected to a puller 905 and the tractor extends along the outer diameter 901 of the catheter. In some variations, the tractor may be infused, bonded or laminated with a stiffening element in part to make it less likely that the tractor collapses in diameter when the dozer catheter is pulled and allows for vacuum applied to the applied to the proximal end of the tractor puller 905 to exert force/vacuum on the clot via the distal end of the assembly, as shown in FIGS. 9B and 9C.

In FIG. 9B, the tractor is coupled to a portion of the tractor puller 905 that is proximal 921 to a distal end of the puller. Thus, as the puller is extended distally, the tip may extend past the distal end of the catheter, prior to inverting the tractor. FIG. 9B also shows an (optional) tractor hold 917

In FIG. 9C, the apparatus includes a stop element attached at or near the distal end of the puller 905. A sliding ring 911 on the tractor may be used to allow the puller to slide distally without pulling on the tractor; only when the puller is withdrawn proximally far enough that the stop 909 engages with the sliding ring 911 does the puller pull the tractor proximally, and invert the tractor over the distal end opening of the catheter, rolling the tractor an pulling in any clot material, which may be aided by the application of vacuum 914 through the puller. Thus, this arrangement may allow the user to extend the tractor puller distally at lengths beyond the distal end of the catheter without pulling the tractor distally.

In any of the variations described herein, including those shown in FIGS. 9A-9C, the apparatus may be coupled to a valve 923 for connection to a vacuum source 914. The vacuum may be connected to the elongate inversion support (e.g., catheter) and/or to the puller, as shown in FIGS. 9A-9C.

Any of the apparatus variations described herein may include a lubricous coatings such as hydrophilic coatings applied on the OD &/or ID of the tractor, on any and all sections, and/or on the outer or inner diameter of the elongate inversion support (e.g., catheter).

In general, the apparatuses described herein may allow delivery of a guidewire and/or a smaller catheter through the outer catheter and tractor, which may be useful for both guidewire operation (for clot access) and also for applying optional vacuum. In addition, the tractors described herein may have minimal to no collapsing when they are inverted inside the outer catheter when under axial tension, which may prevent jamming on the catheter distal tip and may reduce the amount and/or volume of clot that can be extracted. Further, any of the tractors described herein may have adequate coarseness to grab the clot, yet still roll smoothly around the distal annulus. Typically, the tractor does not adversely affect catheter tracking, as it may be extremely flexible and slippery.

As just discussed above, the pre-loaded tractors described herein may not slide with respect to the OD of catheter during vessel access. The tractor may only slide on the OD of catheter when the user pulls the tractor puller.

In general, the user may advance the elongate inversion support (e.g., catheter) forward while holding the tractor puller fixed, thereby enveloping clot in place rather than pulling clot to catheter. Further, the tractor may be biased (e.g., heat-shaped) to a preferred configuration to help grab clot effectively and roll nicely around the catheter tip. In general, the distal end of the catheter (tip) may be stiffer than the catheter section just proximal to the tip (to allow rolling of dozer around tip). The tip may include a lubricious coating. The catheter tip may have a radius of >0.00025", >0.00035", >0.0004", >0.0004", >0.00025", or <0.0005" to allow rolling of tractor more easily. For example, the catheter tip hardness may be greater than >72D, and/or may be formed of a polymeric material such as PTFE, nylon, PEEK, stainless steel, etc.

In some variations, the distal region (e.g., distal 5 cm, 10 cm, etc.) of the catheter allows for tracking through ⅛" diameter radius and also has a limited axial compress to <10% of the distal catheter length during axial compression loads of, e.g., 100 g, 200 g, and 300 g, etc. when pulling in the dozer and grabbing clot.

As mentioned above, any of these apparatuses may allow for the delivery of guidewire and/or smaller catheter through aspiration catheter. In general, the tractor may be configured to have a Poisson ratio <1.5 (e.g., <1.2, <1.1, etc.) when under tension (this helps prevent the tractor from jamming on catheter tip).

In any of the variations described herein, the tractor and/or catheter may be radiopaque. For example, a band or region may be radiopaque. The entire tractor may be radiopaque, e.g., NiTi wire filled with PT or Tantalum (DFT wire) may be used to form the tractor. Alternatively, the proximal and/or distal end of the tractor may have radiopaque markers.

The apparatuses described herein may be used to remove materials such as clots, including to prevent or treat stroke. For example, the apparatuses described herein may be used to track up through the siphon of the carotid artery, which is typically highly tortious. When pulled, the tractor may roll around the catheter distal end without locking up, while still grabbing clot. As mentioned, any of these apparatuses may also work in combination with a vacuum. The use of a vacuum may be unnecessary, but may be beneficial, particularly when initially engaging the clot with the tractor region and/or the distal end of the catheter. Any of the apparatuses described herein may also be configured to grab a clot in a large variety of vessels, including those ranging from 1.5 mm to 3.5 mm, even when the catheter has approximately the same outer diameter as the inner diameter of the vessel, or where the catheter is otherwise corked in the vessel.

Apparatuses Adapted for Use with Aspiration

As mentioned, any of the apparatuses described herein may be adapted for use with a vacuum to apply suction (e.g. aspiration) to assist in clot removal. Although the device may be used without the use of aspiration, in some instances clot removal may be aided by the use of the mechanical atherectomy apparatuses described herein. Furthermore, traditional techniques for removing a clot using aspiration (e.g., using a simple flexible catheter, commonly referred to as an intermediate catheter) may be improved by the use of the mechanical atherectomy apparatuses described herein. Use of aspiration alone often results in clogging of the intermediate (aspiration) catheter and may therefore have trouble removing the entire clot, particularly in the tortious vessels. Any of the apparatuses described herein may be used with an intermediate catheter, and may be adapted for use with vacuum clot removal technique, including being adapted to permit vacuum to be applied while the apparatus is within the lumen of the intermediate catheter, so that aspiration may still be applied from the distal end of the intermediate catheter and/or the apparatus, as well as permitting aspiration to be applied while the apparatus is extended distally from the intermediate catheter. The applied vacuum may aid in initially gasping or grabbing the thrombus. The vacuum may be applied from the distal end of the apparatus and/or of an intermediate or outer catheter or sleeve that is used with the apparatuses (e.g., elongate inversion support and inverting tractor). Also described herein are apparatuses that are adapted for use with a vacuum, including for use with an intermediate or outer catheter through which the apparatus may be delivered to the clot. The apparatus may grab clot from within the outer catheter, or it may be extended distally out of the intermediate or outer catheter. For example, FIGS. 7A-8D, described above and in additional detail below, are examples of elongate inversion supports that may be used in any of the apparatuses described; these elongate inversion supports may be particularly well suited to applying aspiration from the intermediate catheter.

FIG. 11A shows an example of a configuration in which an outer/intermediate catheter or sleeve that is highly flexible may be maneuvered, for example with a guidewire, to a distal end of the device. Thus, the intermediate catheter may be maneuvered near, or adjacent to, the thrombus. As in any of these methods of use described herein, imaging (such as fluoroscopy, contrast imaging, etc.) may be used. Once in positioned, the guidewire may be removed or left in place, and the apparatus including the elongate inversion support and inverting tractor may be extended within the intermediate catheter/sleeve. In FIG. 11A, the intermediate catheter 4104 is shown positioned within the vessel 4109 distally. As with any of the illustrations here, in the vessel may be highly tortious and branching, although for convenience it is shown as straight in the figures. The apparatus 4100 is extended distally through the intermediate catheter, and extends out of the distal opening of the intermediate catheter to grab the clot 4111, as shown. The puller 4105 may thus be drawn proximally (to the left in the figure) to pull the tractor 4103 from over the catheter portion of the elongate inversion support 4113, so that it inverts and rolls into the lumen of the elongate inversion support, capturing and drawing the clot in with it. The clot may be compressed.

Thus, this configuration may be referred to as a vessel cleaner. In addition to the rolling of the tractor to grab and pull the clot, the clot may be pulled by a vacuum applied from one or both of the intermediate catheter 4121 and/or the elongate inversion support 4123. Vacuum may be applied, e.g., within the intermediate catheter, before the apparatus is positioned distally (or even within the intermediate catheter at all) or after it has been extended distally from the intermediate catheter. This configuration shown in FIG. 11A may introduce the tractor through outer catheter to the face of clot. As mentioned, the mechanical thrombectomy apparatus may be extended distally from the intermediate catheter either by pushing it out distally and/or by pulling back the intermediate catheter to deploy all or part of the tractor into vessel, as shown. If vacuum is applied through the catheter, the catheter forming the elongate inversion support may be jacketed or sealed to allow aspiration through this catheter.

Optionally pull vacuum through outer and/or inner and/or puller. As mentioned, thereafter the tractor may be pulled proximally relative to the the elongate inversion support to pull the clot. The intermediate catheter may then be advanced distally and/or the mechanical thrombectomy apparatus may be withdrawn proximally to remove the apparatus once the clot has been removed. Thereafter an angiogram may be taken to confirm that the clot has been removed.

Alternatively, in FIG. 11B, a clot may be removed using the intermediate catheter to draw a vacuum with the mechanical thrombectomy apparatus within the lumen (e.g., near the distal end, but not extending fully from the distal end) of the intermediate catheter. As described for FIG. 11A, in FIG. 11B the intermediate catheter may be inserted into the vessel (e.g., using a guidewire) so that the distal end is positioned near the clot. Suction may be used to draw the clot into the intermediate catheter either before the mechanical thrombectomy device is inserted or after it has been inserted.

In FIG. 11B, the elongate inversion support 4113' is particularly well suited for use with a vacuum applied through the intermediate catheter 4104 surrounding the apparatus. For example, in FIG. 11B, the elongate inversion support 4113' include a distal catheter region 4125 that extends just a few cm from the distal end opening in which the clot is drawn. The elongate inversion support then tapers down to an elongate support, which may be formed by a wire, hypotube or skived region. This configuration may prevent the catheter from blocking the lumen of the intermediate catheter and and therefore increasing the resistance of the vacuum before it can reach the open distal end and apply suction to drawn the clot. Alternatively or additionally, the outer diameter of the catheter portion of the elongate inversion support may be sized to allow more of the vacuum to pass. For example, the apparatus may be sized such that there is at least about 0.002 inches or greater (e.g., 0.003, 0.004, 0.005, 0.006, etc., inches) between the outer diameter of the catheter and the inner diameter of the intermediate catheter ("outer catheter"). This may also permit unimpeded rolling of the tractor over the distal end opening of the elongate inversion support.

In operation, the method of removing clot such as shown in FIG. 11B may include pulling at least the tip of a clot into the intermediate catheter through the use of a vacuum 4121. Typically the clot may clog within the intermediate catheter; the mechanical thrombectomy apparatuses described herein may be used to remove the clot from within the intermediate catheter. For example, while maintaining vacuum, the mechanical thrombectomy apparatus may be inserted (or it may be preloaded in intermediate catheter as mentioned) and the tractor puller 4105 may be pulled to pull the clot out of the intermediate catheter and the vessel, compress and/or macerate it and pull it into the apparatus and therefore the intermediate catheter, where it can be withdrawn proximally, e.g., by removing the mechanical thrombectomy apparatus. As mentioned, an angiogram may be taken through intermediate catheter (e.g., leaving it in place in case the mechanical thrombectomy apparatus needs to be re-inserted and used to remove more clot) to confirm clot has been removed.

As mentioned, a full catheter such as shown in FIG. 11A may block or prevent the vacuum from reaching the distal end of the intermediate vessel. Therefore it may be beneficial to adapt the mechanical thrombectomy apparatus so that it can be used with vacuum within an intermediate catheter or sleeve, as shown in FIG. 11B. This may be achieved as mentioned above, by minimizing the larger-diameter catheter portion of the elongate inversion support forming the distal end opening over which the tractor inverts. Returning now to FIGS. 7A-8D, in FIG. 7A, the elongate inversion support 700 has a distal catheter portion 701 having a larger diameter than the more proximal region 703, and also includes a plurality of openings, holes, gaps, cut-out regions, slots, etc. 709 that may allow the flow of vacuum through the elongate inversion support more easily. The elongate inversion support shown also includes a distal end 707 into which a tractor 711 inverts, as shown in FIG. 7B. IN FIG. 7B, the elongate inversion support is shown transparent so that the puller 713 and tractor within the elongate inversion support is visible.

Similarly, in FIGS. 7B and 7C, the entire length of the elongate inversion support includes a plurality of cut-out regions 713 which may increase the ability to allow the flow of a vacuum or other fluid within the apparatus, but may still allow the elongate inversion support to provide column strength to resist collapsing up to at least 500 g of compressive longitudinal force applied by, e.g., pulling on the tractor. Similarly, the elongate inversion support of FIGS. 7E and 7F show a skived catheter that also includes openings 709 along its length. The puller and tractor 412 are shown within the elongate inversion support in FIG. 7F. FIGS. 7G and 7H illustrate an example in which rather than a skived portion of the catheter, the distal catheter region of the elongate inversion support is formed by a wire, bar, tube, 721 etc., that is attached to the catheter at the distal end. The catheter may also optionally include openings 709. The elongate inversion support of FIGS. 7I and 7J includes openings 709' along all or much of its length (particularly near the distal end region) as shown.

Finally, the variation of the elongate inversion support shown in FIG. 7K includes a minimal catheter portion (cylinder 716) that is connected to a wire, bar, tube, hypotube, skived region, etc. 717.

FIGS. 8A-8D illustrate the operation of a similar minimal elongate inversion support 800. In this example, the apparatus includes a distal aperture 743 bonded securely to a wire, bar, tube, hypotube, skived region, etc. 746 forming an elongate support. The elongate support may be hollow (e.g., may include a lumen for a guidewire) or solid. The elongate support may also include one or more additional support guides 750 as shown in FIG. 8B. These supports may help contain the puller and/or tractor within the elongate inversion support. Any of the elongate inversion supports described herein may include additional support guides. The elongate inversion support of FIG. 8B is shown with a tractor 711 and puller 713 in FIG. 8C. As mentioned, this variation may be particularly well suited for use with an intermediate (e.g., "outer") catheter, sleeve, or the like 809, as shown in FIG. 8D.

Expandable Distal Ends

Figure 12A:
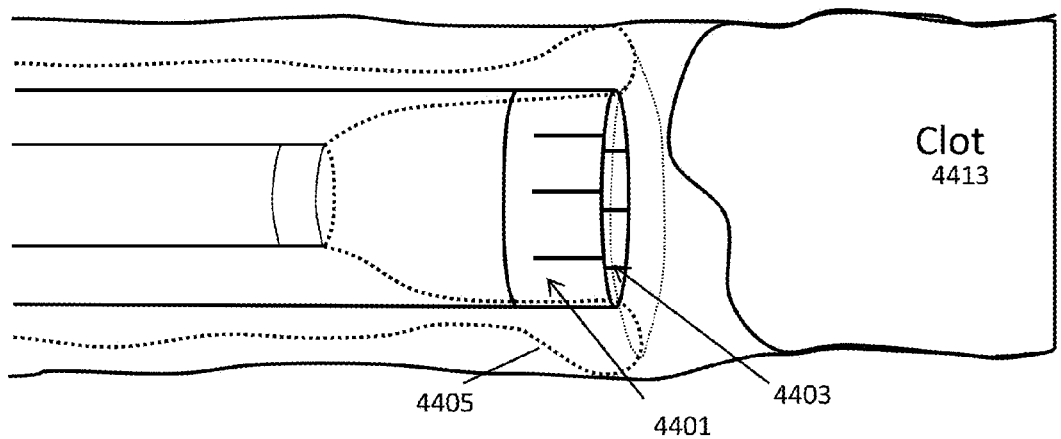
FIGS. 12A-12C illustrates an example of the operation of a mechanical thrombectomy apparatus with an expandable distal end region (e.g., expandable distal end opening in the elongate inversion support.
Figure 12B:
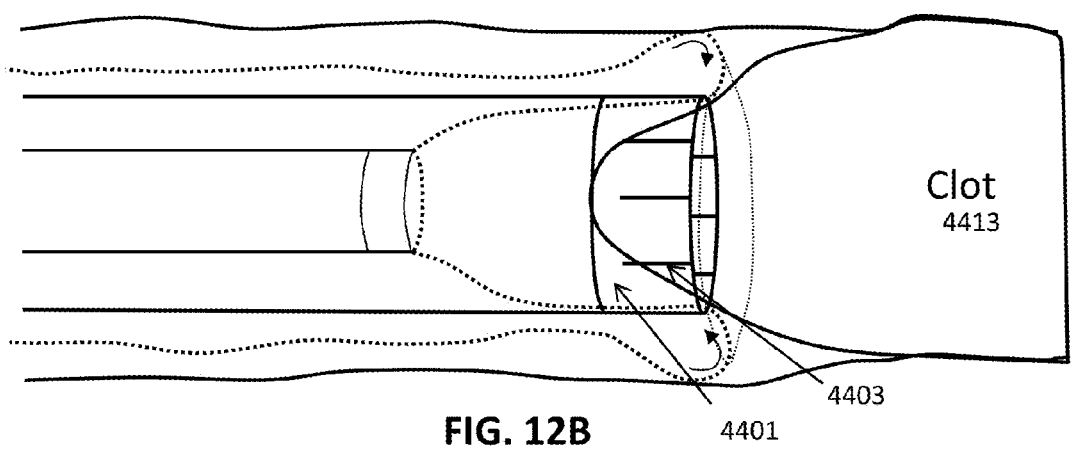
Figure 12C:
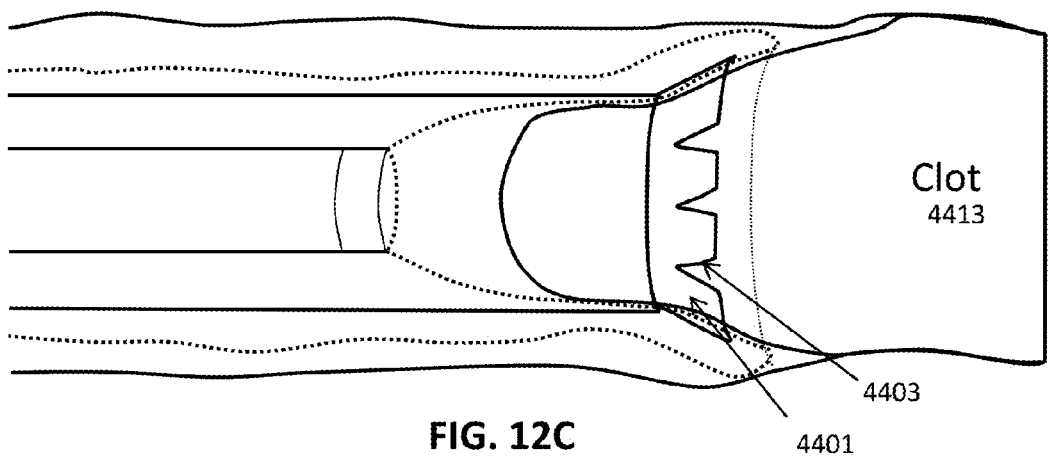

Any of the mechanical thrombectomy apparatuses described herein may include an elongate inversion support having a distal end that is expandable from a smaller diameter aperture (e.g., distal end opening) to a larger-diameter aperture. This expansion may be performed by pulling the clot within the catheter. For example, FIGS. 12A-12C illustrates the operation of an example of an elongate inversion support configured as a catheter having an expandable distal end. In this variation the catheter distal end 4401 may include slots or slits 4403 formed or cut, e.g., by laser-cutting, in the distal end of the catheter of the elongate inversion support. The apparatus may be operated as described above, positioning near (e.g., against or adjacent to) a clot, and pulling proximally on the puller to draw the tractor 4405 into the catheter, as shown in FIG. 12B. Although the apparatuses described herein may generally compress a clot greatly, compression may be made easier and/or more efficient by providing a more gradual decrease in radial diameter. As shown in FIG. 12B, when the tractor is rolled over the distal end opening and inverted, the clot may be drawn in along with the tractor. As the large clot 4413 is brought into the distal end opening, the distal end opening may expand and open along the slots or slits 4403, as shown in FIG. 12C, so that the distal end opening flares out. In some variations an elastic sleeve, gasket, ring or cover (not shown in FIG. 12A-12C) may be included at least partially covering the distal end to prevent the edge from catching the tractor. For example, and elastic or stretchable layer may cover the cut distal end so that the distal end may be opened to form an outward flare. In FIG. 12C the outward-flared distal end is shown forming a funnel-shape into which the clot may be pulled. This funnel-shaped opening may help compress the clot so that it may be drawn into the mechanical thrombectomy apparatus.

In some variations the elongate inversion support may be configured to have, or to assume, a funnel-shape at the distal-facing end. The distal-facing end may always have a funnel-shaped mouth at the distal end opening, or the distal end opening may be configured to assume a funnel shape, as shown in FIGS. 12A-12C. In some variations the distal end of the elongate inversion support is configured to be elastic in a radial directly, but maintain stiffness along the proximal-to-distal axis (in compressive load). For example, the distal end of the elongate inversion support may be configured with strands or rods extending in the proximal-to-distal axis that have a high compressive load strength, but which may separate from each other to enlarge the distal end opening; for example they may be connected by rings in which more distal rings are more elastic/stretchable than more proximal rings.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A mechanical thrombectomy apparatus for removing a clot from a vessel, the apparatus comprising:
    a catheter having a proximal end and a distal end and a distal end opening;
    a tractor comprising a flexible tube that extends within the catheter, inverts over the distal end opening of the catheter and extends over the distal end of the catheter, wherein the tractor is configured to invert by rolling over the distal end opening of the catheter when a first end of the tractor is pulled proximally within the catheter;
    a puller coupled to the first end of the tractor, wherein the puller extends within the catheter to the proximal end of the catheter; and
    a tractor hold attached to an outer surface of the catheter proximal to the distal end of the catheter, wherein the tractor hold secures a second end of the tractor to an outside surface of the catheter, wherein the tractor is fixed to the catheter until a force greater than a threshold force is applied by pulling the first end of the tractor proximally within the catheter
    wherein the threshold force is between 50 g of force and 500 g of force.

2. The apparatus of claim 1, further comprising a guidewire lumen extending through the catheter, the puller and the tractor, and configured to pass a guidewire.

3. The apparatus of claim 1, further wherein the tractor hold does not extend to the proximal end of the catheter.

4. The apparatus of claim 1, wherein the tractor hold extends proximally along the catheter for less than 10 cm.

5. The apparatus of claim 1, wherein the tractor hold compresses the tractor against the catheter.

6. The apparatus of claim 1, wherein the tractor hold is configured to hold the second end of the tractor until the threshold force is applied, wherein the threshold force is between 200 g of force and 500 g of force.

7. The apparatus of claim 1, wherein tractor is biased to expand beyond an outer diameter of the distal end of the catheter in a first relaxed configuration, further wherein the tractor is biased to expand to a second relaxed configuration having an outer diameter that is greater than an inner diameter of the distal end of the catheter, wherein the tractor converts between the first configuration and the second configuration by inverting.

8. The apparatus of claim 1, wherein a proximal end of the tractor hold is attached to the catheter.

9. The apparatus of claim 1, wherein the catheter comprises a larger outer diameter region and a smaller outer diameter region that is proximal to the larger outer diameter region, further wherein the tractor hold secures the tractor at one or more of: over the smaller outer diameter region, and between the larger outer diameter region and the smaller outer diameter region.

10. The apparatus of claim 9, wherein an outer diameter of the tractor hold is flush with the larger outer diameter region.

11. The apparatus of claim 9, further comprising a stepped transition between the larger outer diameter and the smaller outer diameter.

12. The apparatus of claim 1, wherein the tractor hold comprises one or more of: a polyether block amide, a polyolefin, a polyethylene, a polypropylene, a polyethylene terephthalate (PET), and a Polytetrafluoroethylene (PTFE).

13. The apparatus of claim 1, further comprising a tractor lock on the second end of the tractor, wherein the tractor lock engages with the tractor hold to secure the tractor lock on a proximal side of the tractor hold until the threshold force is applied by pulling the first of the tractor proximally within the catheter.

14. The apparatus of claim 13, wherein the tractor lock comprises a band configured to slide over the outer surface of the catheter.

15. The apparatus of claim 13, wherein the tractor hold comprises a projection extending from the outer surface of the catheter.

* * * * *